United States Patent [19]
Grundfest et al.

[11] Patent Number: 5,662,587
[45] Date of Patent: Sep. 2, 1997

[54] ROBOTIC ENDOSCOPY

[75] Inventors: Warren Scott Grundfest, Los Angeles; Joel W. Burdick, IV; Andrew Brett Slatkin, both of Pasadena, all of Calif.

[73] Assignees: Cedars Sinai Medical Center, Los Angeles; California Institute of Technology, Pasadena, both of Calif.

[21] Appl. No.: 291,428

[22] Filed: Aug. 16, 1994

Related U.S. Application Data

[63] Continuation-in-part of Ser. No. 945,806, Sep. 16, 1992, Pat. No. 5,337,732.

[51] Int. Cl.$^6$ ........................... A61B 1/04
[52] U.S. Cl. .................... 600/114; 600/116; 600/139; 600/115
[58] Field of Search .................... 600/114, 115, 600/116, 117, 118, 139, 143, 144, 151; 604/95

[56] References Cited

U.S. PATENT DOCUMENTS

| | | |
|---|---|---|
| 2,855,934 | 10/1958 | Daughaday, Jr. . |
| 3,279,460 | 10/1966 | Sheldon . |
| 3,895,637 | 7/1975 | Choy . |
| 4,066,070 | 1/1978 | Utsugi . |
| 4,148,307 | 4/1979 | Utsugi . |
| 4,176,662 | 12/1979 | Frazer . |
| 4,207,872 | 6/1980 | Meiri et al. . |
| 4,389,208 | 6/1983 | LeVeen et al. . |
| 4,447,227 | 5/1984 | Kotsanis . |
| 4,491,865 | 1/1985 | Danna et al. . |
| 4,577,621 | 3/1986 | Patel . |
| 4,653,476 | 3/1987 | Bonnet . |
| 4,676,228 | 6/1987 | Krasner et al. . |
| 4,690,131 | 9/1987 | Lyddy, Jr. et al. . |
| 4,706,655 | 11/1987 | Krauter . |
| 4,713,985 | 12/1987 | Ando ............................ 78/804 |
| 4,838,859 | 6/1989 | Strassmann . |
| 4,934,786 | 6/1990 | Krauter . |
| 4,964,062 | 10/1990 | Ubhayakar et al. ................ 364/513 |
| 5,018,509 | 5/1991 | Suzuki et al. . |
| 5,196,017 | 3/1993 | Silva et al. . |
| 5,398,670 | 3/1995 | Ortiz et al. ........................ 600/114 |
| 5,443,440 | 8/1995 | Tumey et al. ..................... 601/152 |

*Primary Examiner*—Linda C. Dvorak
*Assistant Examiner*—Beverly M. Flanagan
*Attorney, Agent, or Firm*—Lyon & Lyon

[57] ABSTRACT

A robot for performing endoscopic procedures in flexible and curved human or animal lumens. A plurality of segments are attached to each other. Traction segments embrace the lumen walls. Other segments include actuators that cause the endoscope to locally deform its shape via bending, extending, or some combination of bending and extension. A method is provided to sequence the action of the segments to cause inchworm-like or snake-like locomotion, or a combination of them through a curved and flexible lumen. The method of movement can be adapted to the lumen characteristics, or to obviate a component failure. A compressed gas line attached to the back segment provides compressed gas for insufflation of the lumen, and can optionally be used to drive the actuators that control the operation of the endoscope segments. The lead segment may include television cameras, ultrasound transducers, biopsy arms, drug delivery systems, or other sensors, diagnostic aids, therapeutic devices, and surgical tools. Medical instruments and sensors can also be placed in the rear or middle segments.

25 Claims, 43 Drawing Sheets

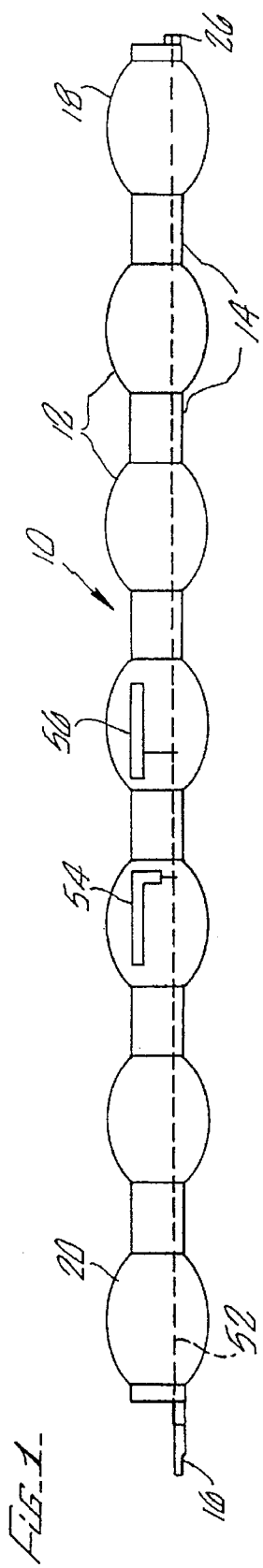
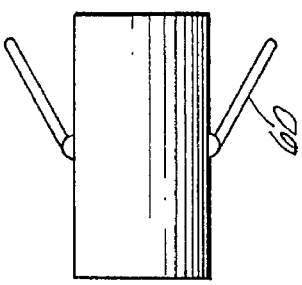
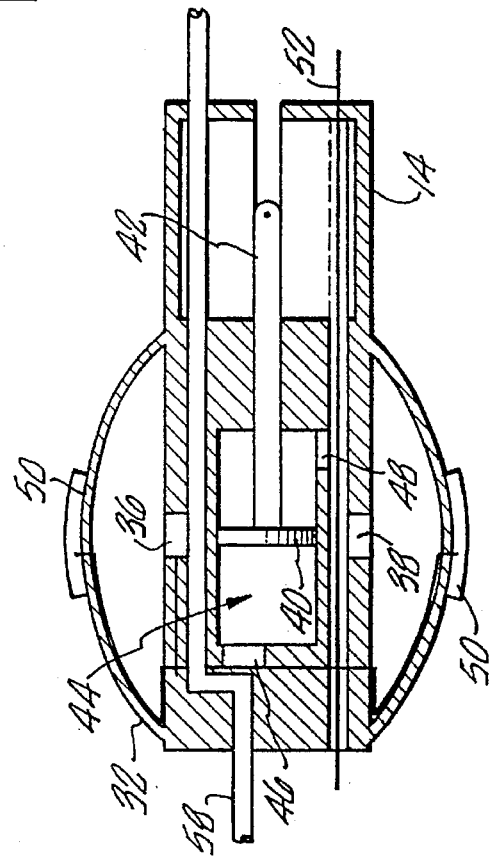
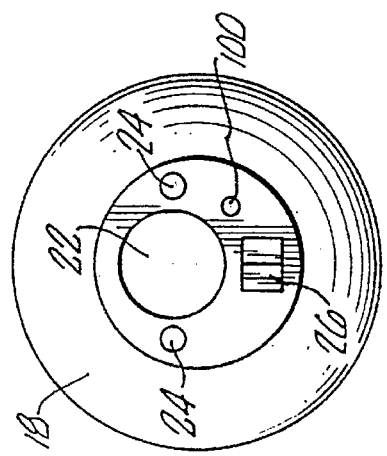

Side View
Traction module contracted

End View
Traction module contracted

Side View
Traction module extended

End View
Traction module extended

Side View
Traction module
contracted

End View
Traction module
contracted

Side View
Traction module
extended

End View
Traction module
extended

End View

Traction Modules
expanded

End View

Traction Modules
expanded

Section A-A
Traction module contracted

End View
Traction module contracted

Section B-B
Traction module extended

End View
Traction module extended

End View

End View

Section A-A
Traction module
contracted

End View
Traction module
contracted

Section B-B
Traction module
extended

End View
Traction module
extended

Side View

Traction Module contracted

End View

Traction Module contracted

Side View

Traction Module expanded

End View

Traction Module expanded

End View
Traction Modules expanded

End View
Traction Modules expanded

Side View
Traction Module
contracted

End View
Traction Module
contracted

Side View
Traction Module
expanded

End View
Traction Module
expanded

End View

Traction Modules expanded

End View

Traction Modules expanded

Side View

Traction Module contracted

End View

Traction Module contracted

Side View

Traction Module expanded

End View

Traction Module expanded

End View
Traction Modules expanded

End View
Traction Modules expanded

Side View
Traction Module contracted

End View
Traction Module contracted

Side View

Traction Module expanded

End View

Traction Module expanded

End View

Traction Modules expanded

End View

Traction Modules expanded

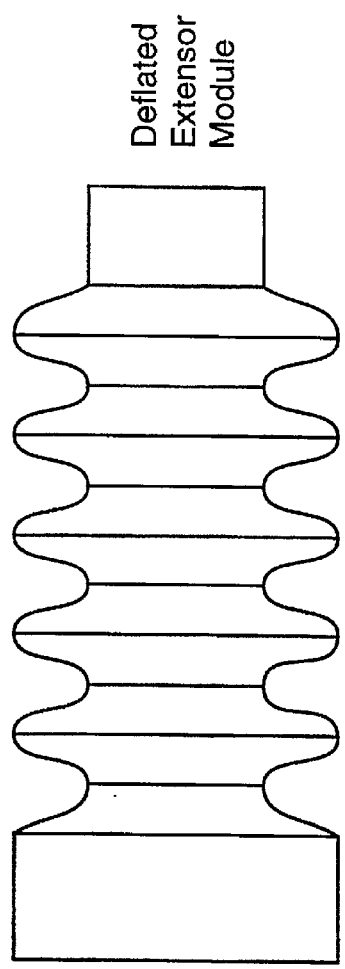
Fig. 58. Deflated Extensor Module
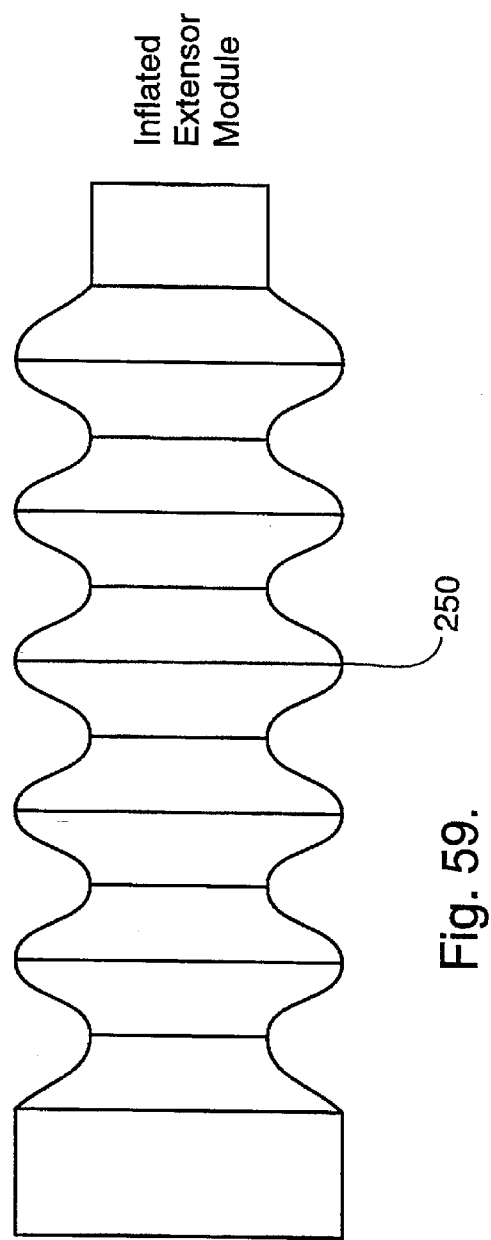
Fig. 59. Inflated Extensor Module

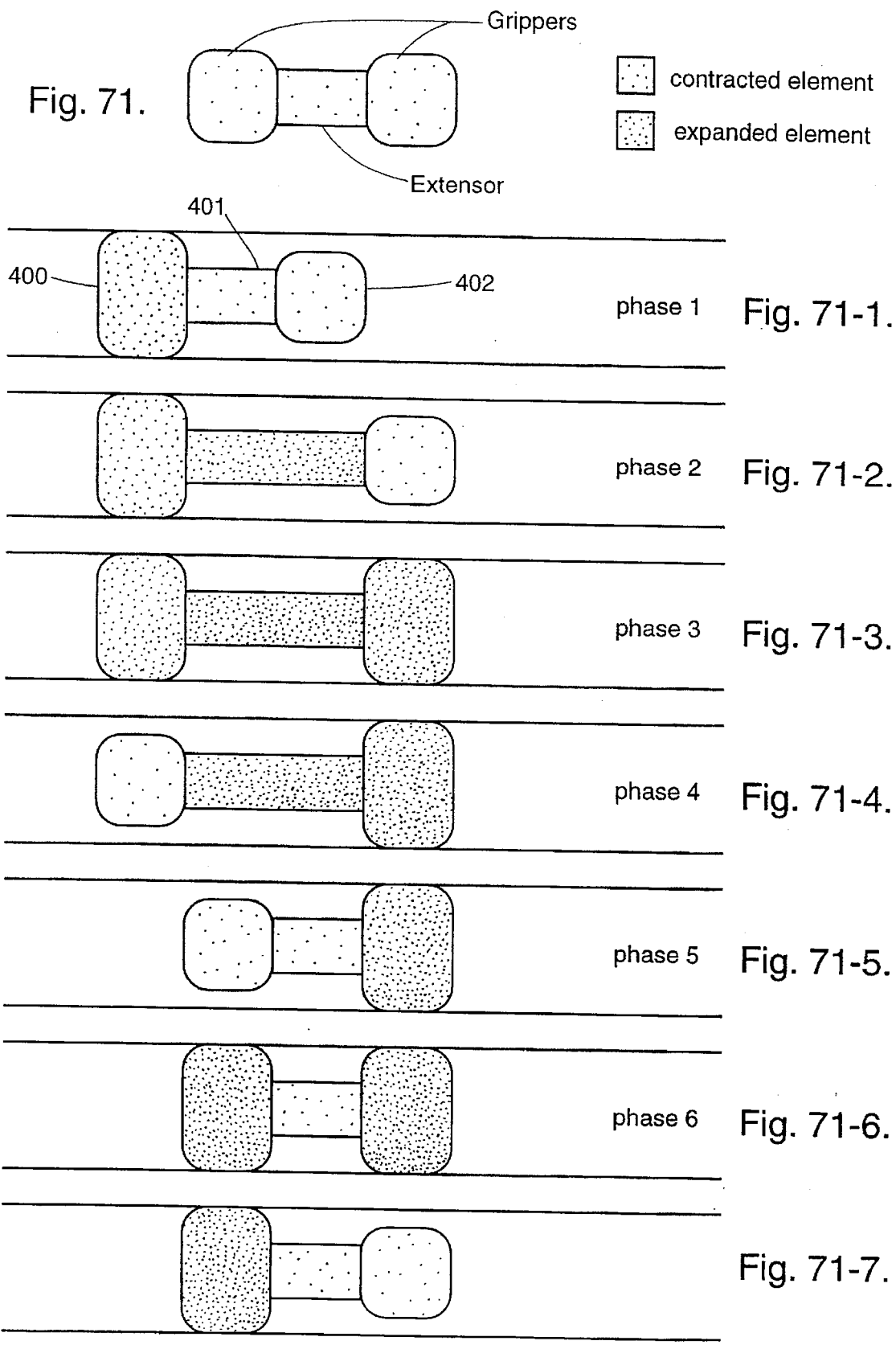

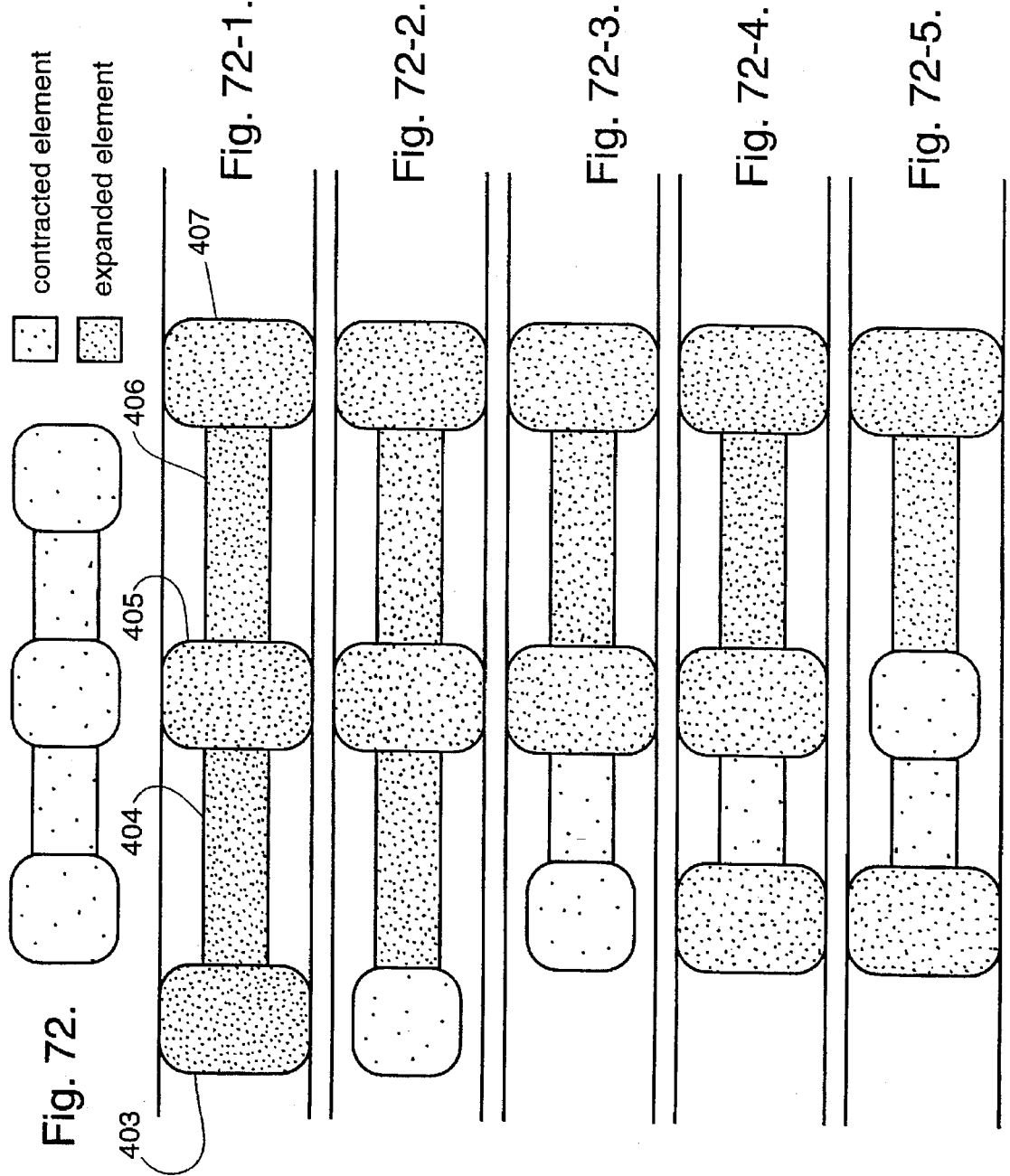

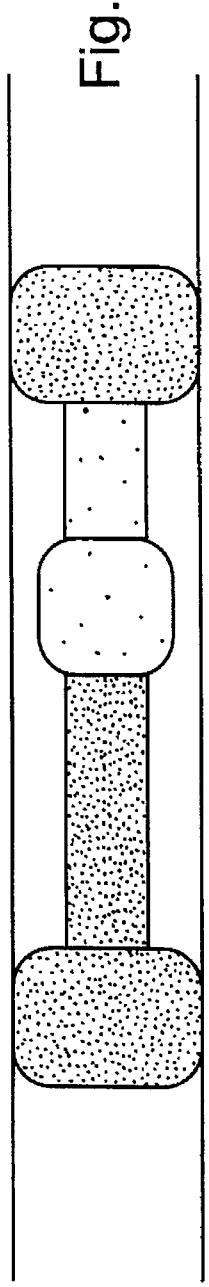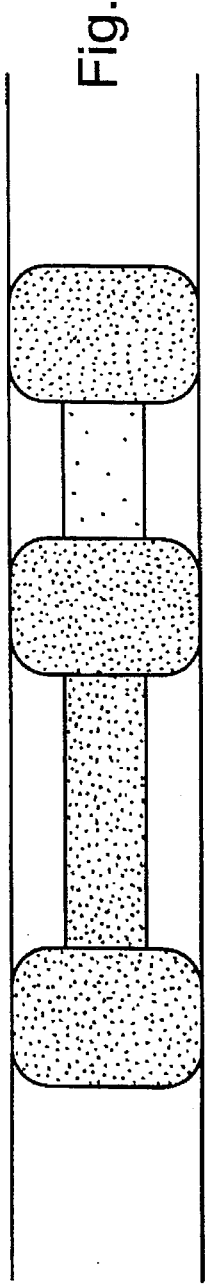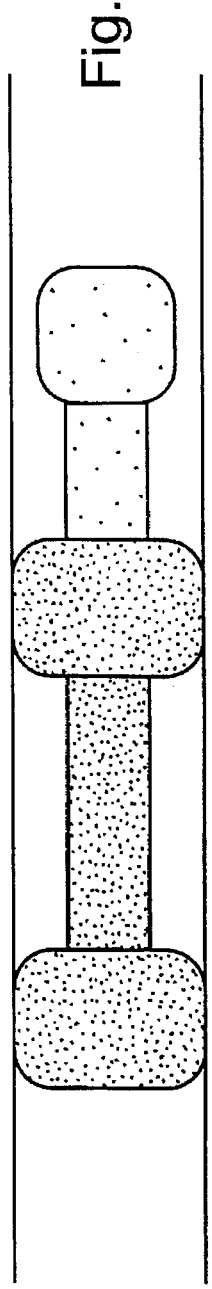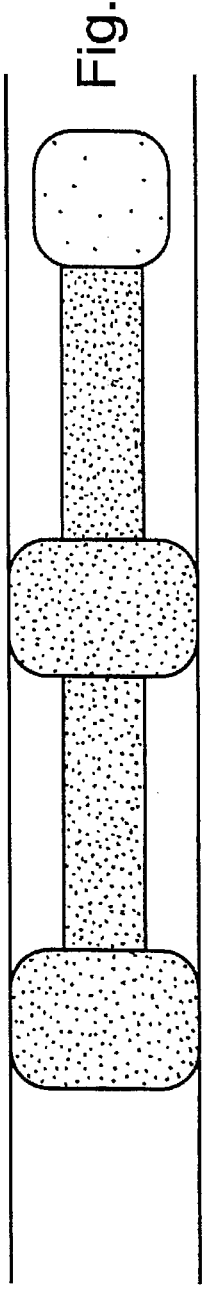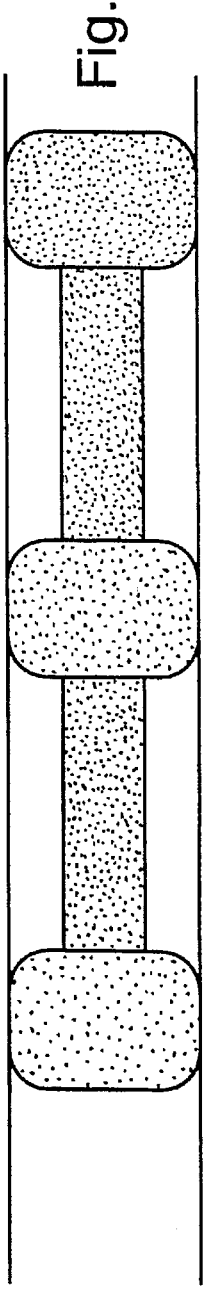
Fig. 72-6. Fig. 72-7. Fig. 72-8. Fig. 72-9. Fig. 72-10.

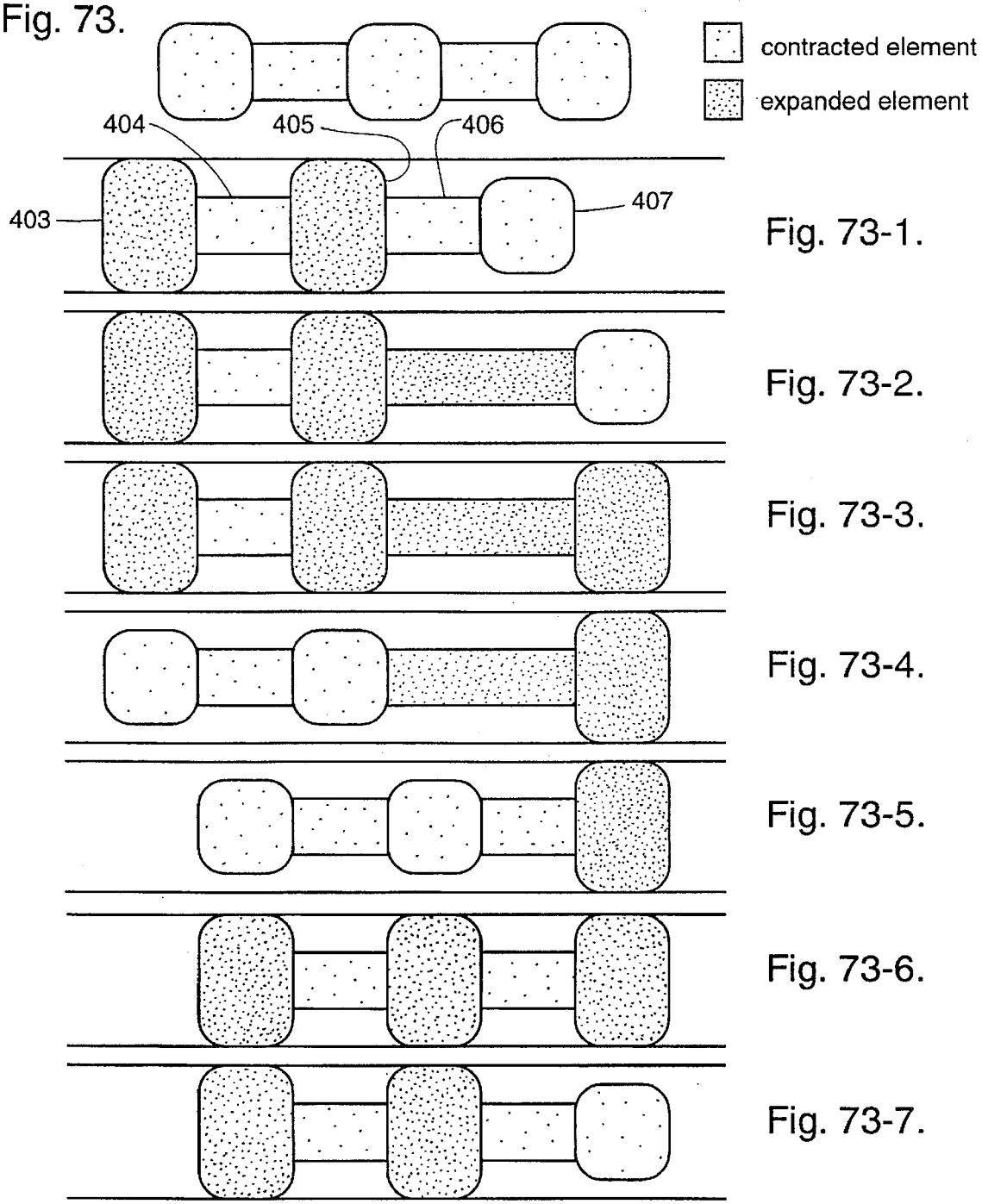

contracted element
expanded element

□ contracted element
▨ expanded element

Fig. 75-1. phase 1
Fig. 75-2. phase 2
Fig. 75-3. phase 3
Fig. 75-4. phase 4
Fig. 75-5. phase 5
Fig. 75-6. phase 6

Fig. 76-4. time step 4
Fig. 76-5. time step 5
Fig. 76-6. time step 6

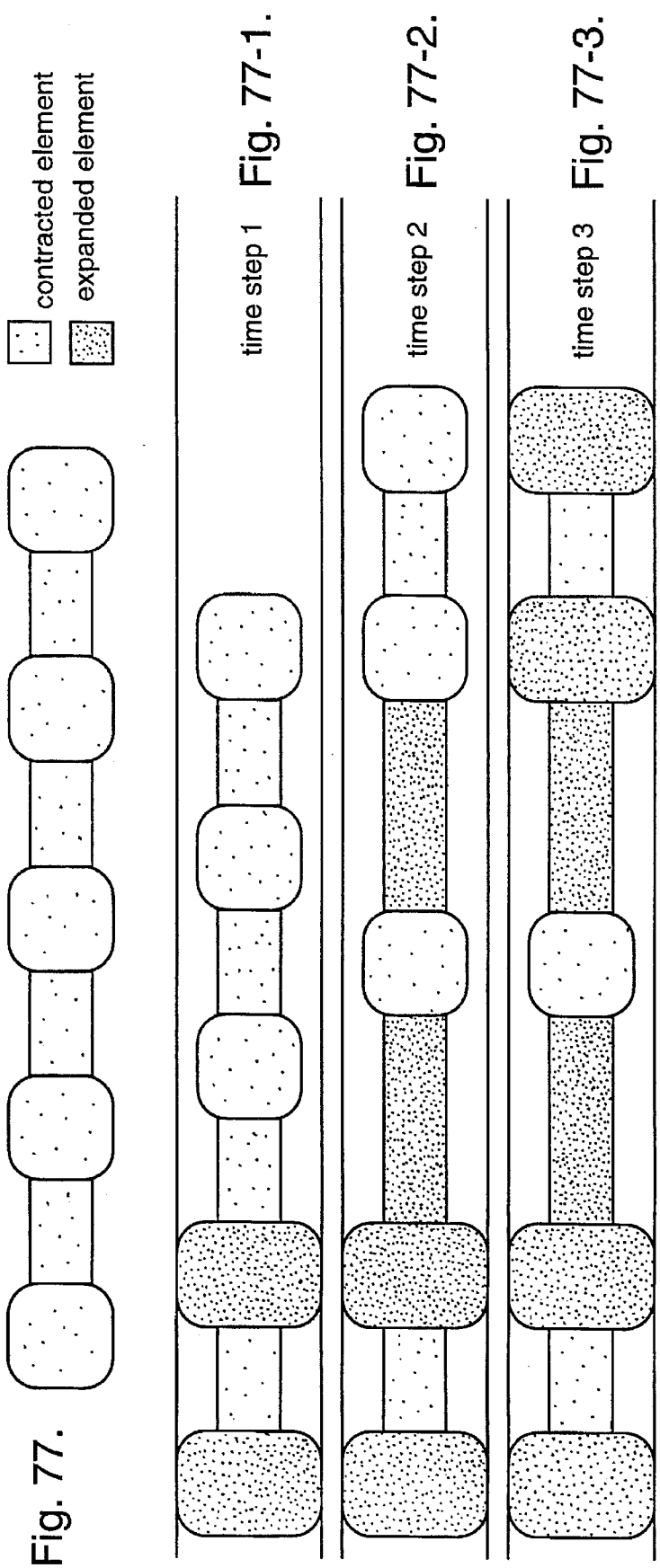

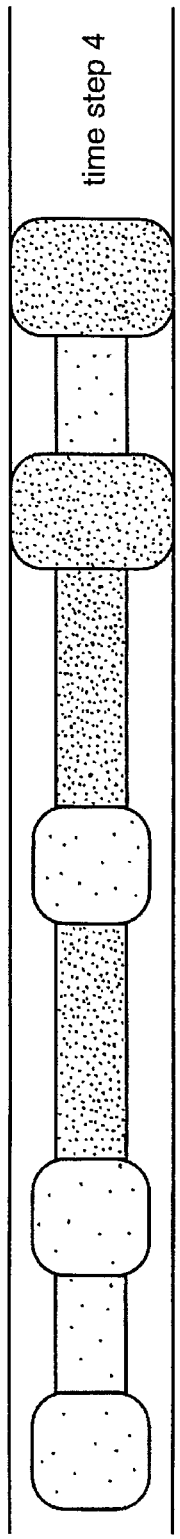
Fig. 77-4. time step 4
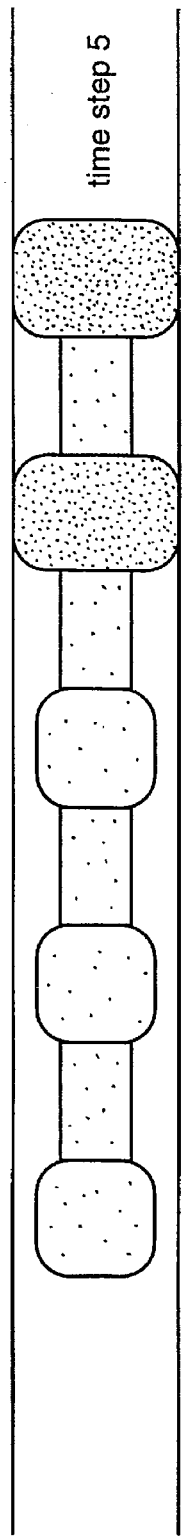
Fig. 77-5. time step 5
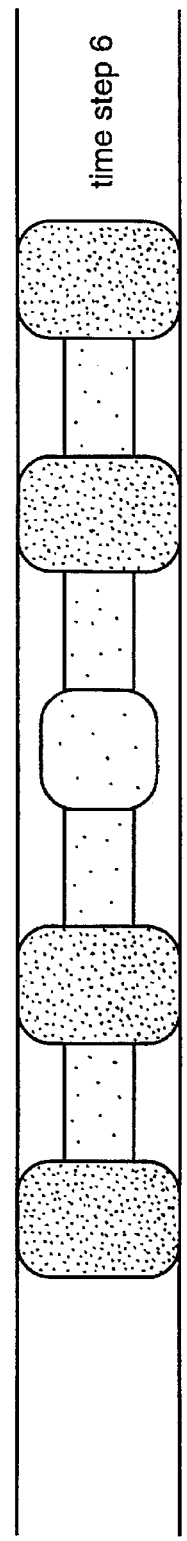
Fig. 77-6. time step 6
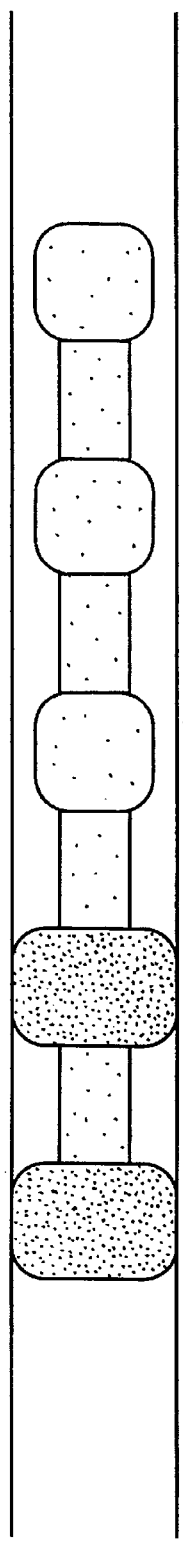
Fig. 77-7.

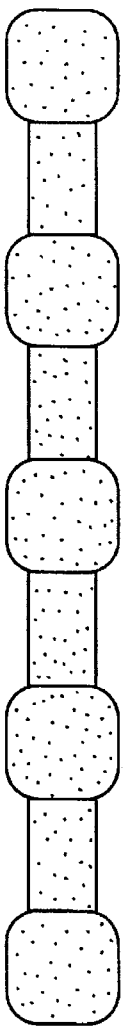
Fig. 78.
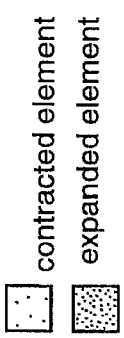
contracted element
expanded element
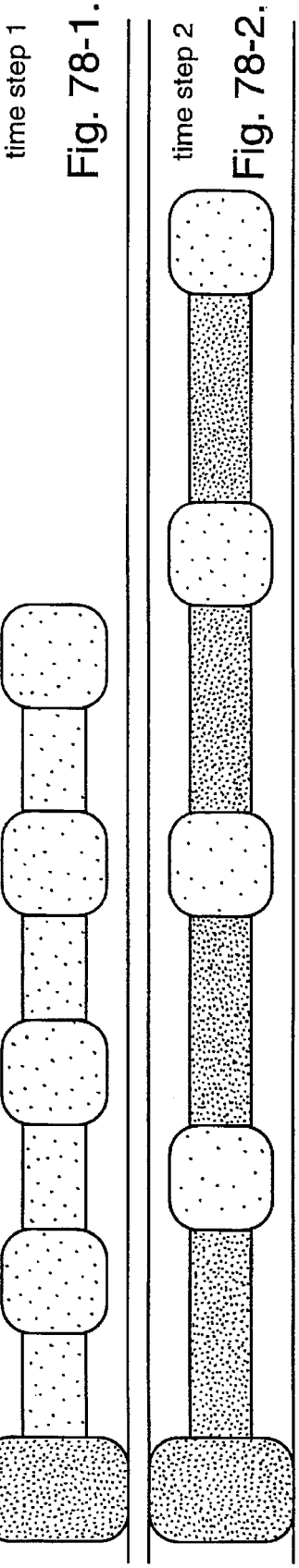
time step 1
Fig. 78-1.
time step 2
Fig. 78-2.
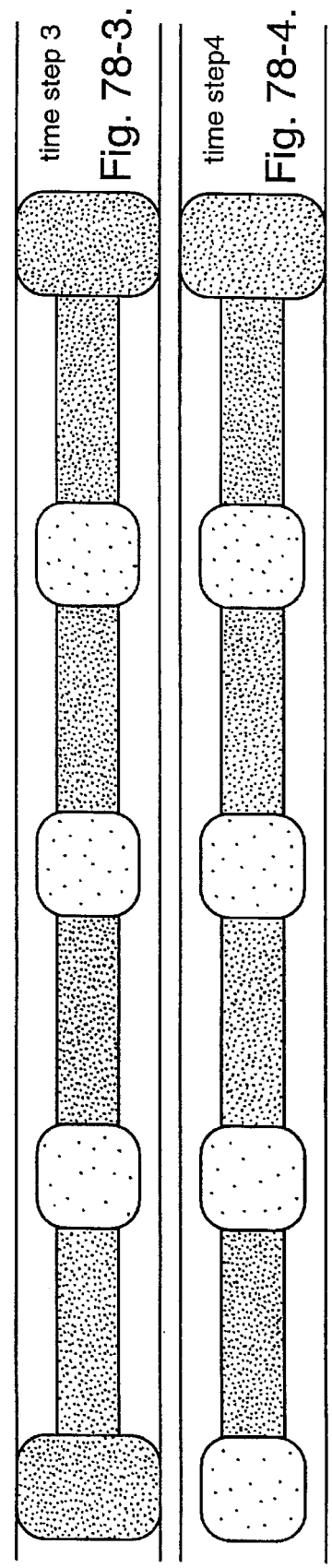
time step 3
Fig. 78-3.
time step 4
Fig. 78-4.

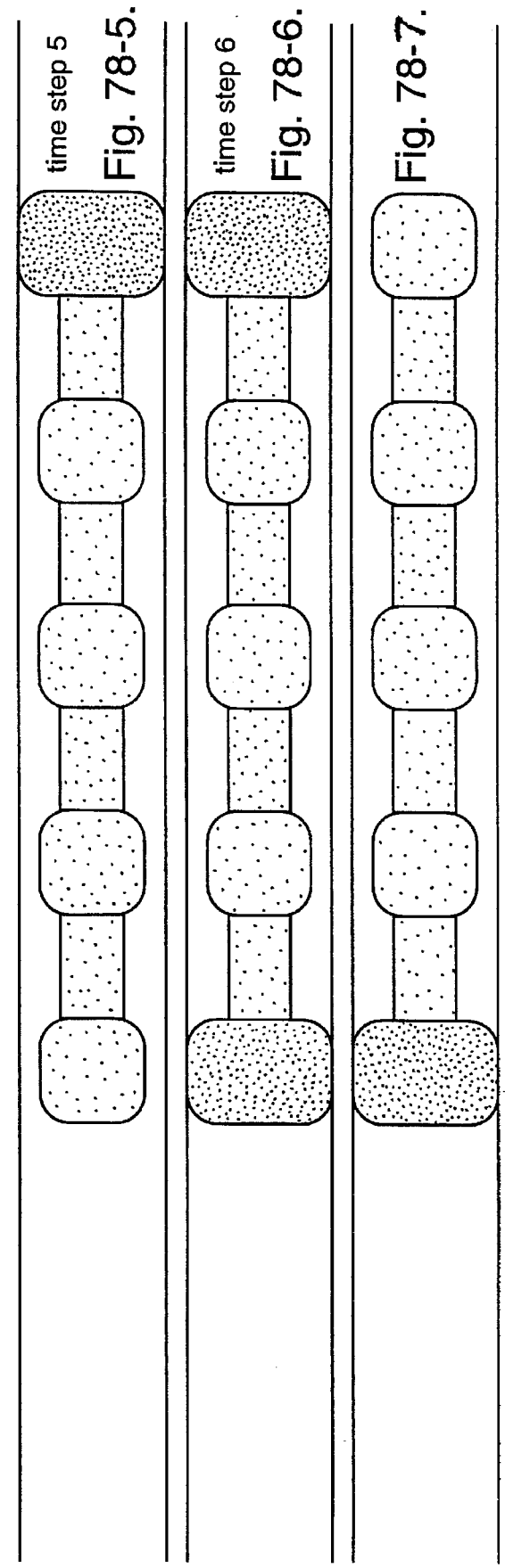

Phase 1

Phase 2

Phase 3

Phase 4

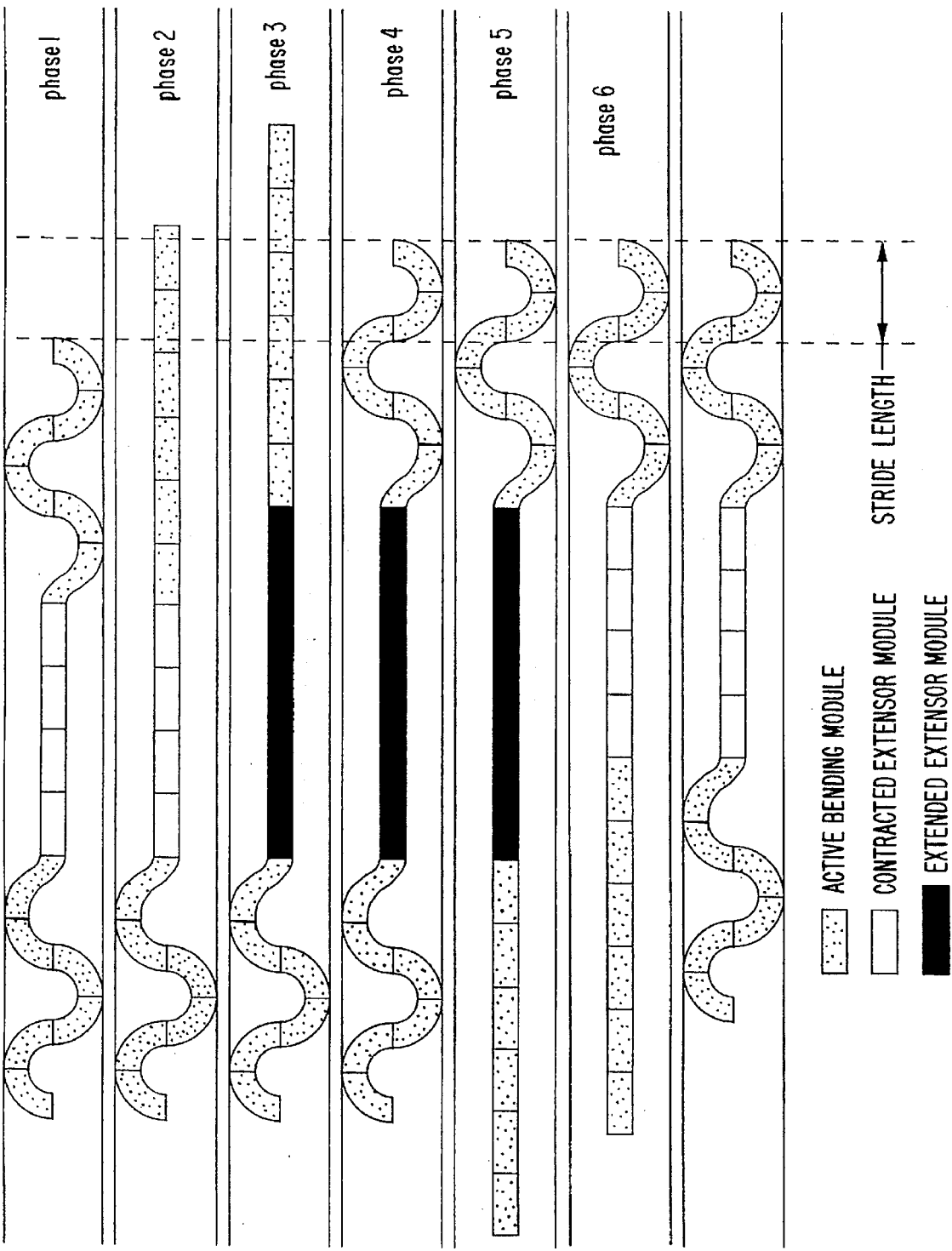

ROBOTIC ENDOSCOPY

This application is a continuation-in-part of our Ser. No. 07/945,806, filed Sep. 16, 1992, and issued on Aug. 16, 1994 as U.S. Pat. No. 5,337,732.

The U.S. Government has a paid up license in this invention and the right in limited circumstances to require the patent owner to license others on reasonable terms as provided for by the terms of U.S. Navy Contract No. N00014-92-J-1920 awarded by the Office of Naval Research.

BACKGROUND OF THE INVENTION

The field of the invention is endoscopy.

Minimally invasive medical techniques are aimed at reducing the amount of extraneous tissue which must be damaged during diagnostic or surgical procedures, thereby reducing patient recovery time, discomfort, and deleterious side effects. Arthroscopic knee surgery is the most widely known example.

A shift to minimally-invasive medical surgery is expected to be one of the biggest trends in medical practice in the 1990's. There are tremendous incentives for the medical community to adopt these techniques. Approximately 21,000,000 surgeries are now performed each year in the United States. It is estimated that 8,000,000 of these surgeries can potentially be performed in a minimally invasive manner. However, only about 1,000,000 surgeries currently use these techniques, due in part to limitations in minimally invasive surgical technology.

Advances in minimally invasive surgical technology could have a dramatic impact. The average length of a hospital stay for a standard surgery is 8 days, while the average length for the equivalent minimally invasive surgery is 4 days. Thus, the complete adoption of minimally invasive techniques could save 28,000,000 hospital days and billions of dollars annually in hospital residency costs alone. Patient recovery times, patient discomfort, surgical side effects, and time away from work are also reduced with minimally invasive surgery.

Most current minimally invasive medical, surgical and diagnostic techniques can generally be classified into two categories: laparoscopy and endoscopy.

A laparoscope is used for minimally-invasive inspection and surgery inside the abdominal cavity. Currently, laparoscopic instruments are generally simple unarticulated tools which are inserted into the abdominal cavity via a hole in the abdominal wall. The laparoscope tip is mounted with simple surgical tools, such as scissors, clamps, tissue samplers, or cauterizers.

An endoscope is a highly flexible device for non-invasive inspection in interior cavities, canals (such as the colon), vessels, etc. Current endoscopes are comprised mainly of a fiber optic bundle for transmitting an optical image, and perhaps some simple mechanism for steering the tip of the endoscope. Their fiber optic bundles can also transmit laser beams which can cut, cauterize, or vaporize tissue. In some endoscopes, tools, such as snares, needles, or probes can also be introduced via an internal lumen within the endoscope. The term laparoendoscopic refers to the collection of these minimally invasive surgical techniques.

Endoscopic diagnosis and surgery are performed by inserting an endoscope through a natural or surgically produced orifice into the colon, arteries, or other interior ducts. Endoscopes are more often used for inspection of interior cavities, though laser surgery is increasingly prevalent. For example, endoscopic lasers have been used to pulverize and remove kidney stones. While there have been some dramatic successes with laparoscopic and endoscopic surgery, the current state of the art in laparoscopic and endoscopic design technology, and function remains quite primitive.

There are a number of disadvantages with current laparoendoscopic technology. Commercial endoscopes, while highly flexible, have only limited steering ability. They are difficult to position and cannot traverse tight bends in the intestine (or other interior ducts, such as arteries). Consequently, about 60% of the gastrointestinal track is unreachable with current endoscope technology. As a result, many diagnostic and surgical procedures in the gastrointestinal track require large abdominal incisions. Further, sudden changes in the internal anatomical structure, such as stomach or colon cramping, are not easily accommodated with current endoscopes.

One of the biggest impediments to the expansion of minimally invasive medical practice is lack of access to interior cavities. In all types of current minimally invasive approaches, the diagnostic and surgical tools are long, thin devices which are inserted into naturally or surgically produced orifices. However, current devices are extremely limited in their mobility and ability make tight bends and to negotiate complex interior structures.

SUMMARY OF THE INVENTION

Hyper-redundant robots are a special class of kinematically redundant (or simply, redundant) robot manipulators which can have actively controlled geometries. Redundant robots possess more than the minimum number mechanical of degrees of freedom (or joints) required to accomplish nominal tasks. Practically, redundant robots have seven or more internal degrees of freedom. Kinematic redundancy can improve robot versatility in complex environments, where the extra degrees of freedom (joints) can be used for obstacle avoidance, or to overcome deficiencies arising from kinematic, mechanical, and other design limitations inherent in non-redundant manipulators.

Hyper-Redundant robots have a very large degree of kinematic redundancy. These systems are analogous in morphology and operation to "snakes," "elephant trunks," "tentacles" or "earthworms". Because of their highly articulated structures, hyper-redundant robots are superior for applications and operation in very complicated and unusual environments.

The present invention is directed to a robot for performing endoscopic procedures. To this end, an endoscopic robot includes a plurality of segments attached to each other. Actuators cause the segments to move together and apart, and to change the angular orientation between segments, inflatable balloons arms, shells, wires, or other elements, around or on the segments provide traction for propulsion by engaging or pushing against the lumen or organ walls.

Accordingly, it is an object of the present invention to provide a robotic endoscope and methods for its movement in a flexible lumen.

BRIEF DESCRIPTION OF THE DRAWINGS

Other objects and features of the present invention will become apparent from the following detailed description taken in connection with the accompanying drawings which disclose several embodiments of the invention. It is to be understood, however, that the drawings are designed for the purpose of illustration only and are not intended as a definition of the limits of the invention.

In the drawings, wherein similar reference characters denote similar elements throughout the several views:

FIG. 1 is a schematically illustrated side elevation view of the present endoscopic robot;

FIG. 2 is a front end view of thereof;

FIG. 3 is a partial section view of one segment of an embodiment of the robot of FIG. 1;

FIG. 5 is a schematically illustrated side elevation view of a segment with articulated arms;

FIG. 8 is a schematically illustrated side elevation view of another embodiment of a robot segment having bow wires;

FIG. 58 is a side elevation view of a deflated extensor module with passive lateral bending capability;

FIG. 59 shows the module of FIG. 58 in the inflated condition;

FIG. 71 through FIGS. 71-7 are schematic illustrations of an inchworm gait of a two-gripper/one-extensor embodiment;

FIG. 72 through FIG. 72-10 are schematic illustrations of locomotion of inchworm locomotion of a three-gripper/two-extensor embodiment;

FIG. 73 through FIGS. 73-7 is a schematic illustration of a second example of a distinct gait for a three-gripper/two-extensor embodiment;

FIG. 74 through FIGS. 74-7 is a schematic illustration of another example of a distinctive gait for a three-gripper/two-extensor embodiment;

FIG. 75 through FIGS. 75-7 is a schematic illustration of yet another gait for a three-gripper/two-extensor embodiment;

FIG. 76 through FIGS. 76-7 is a schematic illustration of a possible gait for a five-gripper/four-extensor embodiment;

FIG. 77 through FIGS. 77-7 is a schematic illustration of another possible gait for a five-gripper/four-extensor embodiment;

FIG. 78 through FIGS. 78-7 is a similar schematic illustration showing another possible gait for a five-gripper/four-extensor embodiment;

FIG. 79-1 through FIGS. 79-12 are schematically illustrated perspective views of a concertina gait for an embodiment having a plurality of lateral deformer modules or segments; and FIG. 80-1 through FIGS. 80-7 is a schematic illustration of a combination gait.

DETAILED DESCRIPTION OF THE PREFERRED EMBODIMENTS

Figure 74:
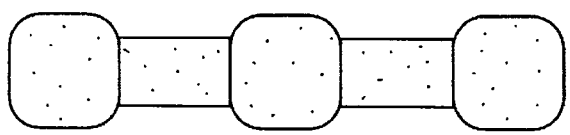
Figures 1, 74:
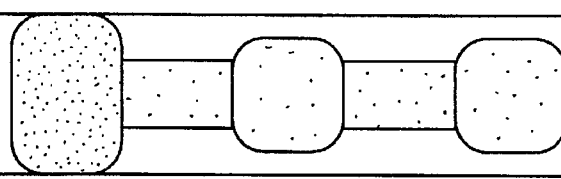

Turning in detail to the drawings, as shown in FIG. 1, an endoscopic robot 10 has a front or lead segment 18, a back segment 20, and a plurality of middle segments 12. Bellows 14 extend in between the segments. A compressed gas (e.g., $CO_2$ or air) supply hose 16 is attached to the back segment 20.

Figures 2, 74:
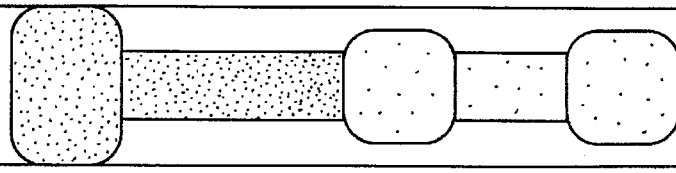

Referring to FIG. 2, the lead segment 18 includes a video camera 22, a pair of spaced apart lights 24 and a retracted biopsy tool with integral tissue storage cavity 26 and an insufflation port 100. Other surgical instruments may also be provided on the lead segment 18 including e.g., a laser, a needle, probe, or other tools that are conventionally used in endoscopy. The lead segment may also contain a drug delivery system. In some embodiments, the lead segment may also contain other diagnostic aids, such as sensors to measure pH and temperature, or ultrasonic transducers. In fact, drug delivery devices and diagnostic devices can also be located in the rear segment 20 or in any middle segment 12.

Figures 3, 74:
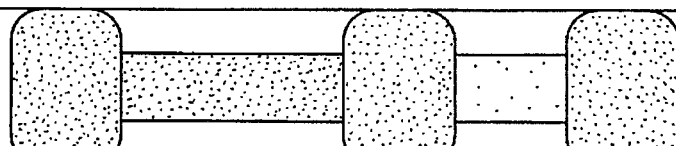
Figures 4, 74:
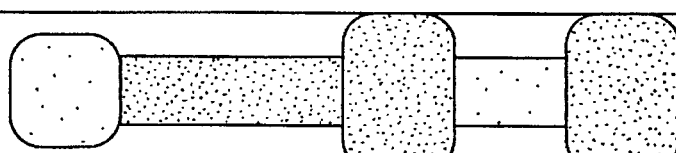

Referring to FIGS. 1 and 3, an inflatable balloon 32 is attached around the outside of each segment. The balloon 32 is preferably toroidal. Within some or all of the segments is a cylinder 44 slidably containing a piston 40 having a joint link 42 extending to an adjacent segment. The joint is preferably either a pin or ball joint. A compressed gas line 58 linked to the supply hose 16 connects to an extend valve 46 and a retract valve 48 to control flow of a compressed gas into the cylinder 44 on either side of the piston 40. Valves 46 and 48 are individually controlled within each segment which has a piston and cylinder actuator. Similarly, pairs of inflation valves, e.g., 36 and 38 individually control flow of compressed gas from the compressed gas line 58 into each balloon 32 on each segment. Pressurized fluid may be used in place of compressed gas.

A control bus 52 extends through the robot 10 and is linked to the balloon inflation valves, as well as the valves 46 and 48 controlling movement of the piston 40. The bus 52 connects to a controller 54 and a receiver/transmitter 56. Tactile sensors 50 may be provided on the inflatable balloons and are also linked to the bus 52. The sensors 50 may measure the stresses placed on the lumen walls, since overloading the lumen tissue could cause injury to the patient. In addition, a means of measurement of the effective diameter of the segment or module may also be used. Other on-board microsensors, including PH sensors, or sensors for detecting enzymes, proteins or bacteria, or for measuring temperature or pressure may also be attached to the balloons.

In operation, the robot 10 is inserted into a body cavity or lumen such as the throat, upper or lower gastro-intestinal tracts, urinary track or biliary tract, either alone or with other endoscopic systems. The robot 10, moves forward through the lumen under its own power with inchworm movements, concertina movements, or movements using a combination of them. The inchworm movement is achieved by temporarily bracing one or more segments against the lumen wall by selectively inflating some or all of the balloons 32, to prevent slippage, and by extending and contracting the segments together via the piston 40 and joint link 42 driven by compressed gas admitted into the cylinder 44 at appropriate times by the valves. The brace points in contact with the environment can be moved or adjusted as needed, while robot segments not in contact with the environment can be controlled to move the robot as desired.

With multiple actuators between the segments, the robot can be controlled to propel itself or crawl through a lumen in either an inchworm mode, or in a concertina (snake-like) mode, to move forward or backward through the lumen. The concertina mode is especially useful where the diameter of the lumen exceeds the diameter of the fully expanded balloons on the segments. For example the diameter of the small and large intestines can vary by a factor of three along its length, inch-worming motion suitable for the small diameter portion of the intestine may not work for the large diameter sections, where concertina motion may be necessary. The robot 10 is controlled to fluidly transition from one locomotion scheme to another to adapt to the local changes in the environment.

The robot 10 may, for example, be delivered to the duodenum by a gastroscope. The robot 10 will then detach from the gastroscope and under its own propulsion system, move through the small intestine to a point of interest for diagnostic or therapeutic surgery functions. The supply hose 16 trails behind the robot 10 to supply compressed gas, which may be used as the driving medium. Using compressed air or gas to power the robot 10 is advantageous because compressed air is required for the endoscopy to insufflate or inflate the lumen ahead of the robot using insufflation port 100. In addition, air can be provided to the robot by a trailing hose which is fabricated from a dissolvable material, such as poly-glycolic acid derivatives. Once the robot has existed from the lumen, e.g., a gastrointestinal track, the air supply hose can be left inside the body, where it will dissolve within a day or two.

The controller 54 controls the valves for the cylinders and balloons using either predetermined sequences or as instructed by the surgeon and transmitted to the controller 54 via a transceiver outside of the patient's body through the transceiver 56 within the robot 10. Alternatively, the transceivers can be replaced with a trailing fiber-optic or metal wire control cable. Batteries within the robot 10 power the controller 54, transceiver 56 and the valves. The transceiver 56 can transmit images from the video camera 22 back to a monitor outside of the body through the transceiver 56. In an alternative embodiment, the piston 40 and cylinder 44 may be replaced with electrically driven actuators. A rear-looking imaging system, including ultrasound, may also be provided on the end segment 20.

The lead segment 18, with or without the biopsy arm 26 may also include devices to wash and dry the lens of the camera 22, irrigation capability, coagulation capability, optical spectroscopy, myographic recording, LIRS, as well as other probes or sensors. The biopsy tool can separately obtain biopsy samples from known and recorded locations and store them within the storage cavity 26 for testing after the robot 10 is removed from the patient. Correspondingly, a delivery device on the robot can deposit or deliver drugs at a target location within the body. Control of such devices can be effected through the control bus 52.

In another application, one or more of the robots 10 may be used in a manner analogous to a "tugboat" to pull a fiber optic cable much deeper into the intestines than is currently possible with endoscopes. Once in position, the fiber can be used for laser based surgery.

Figures 5, 74:
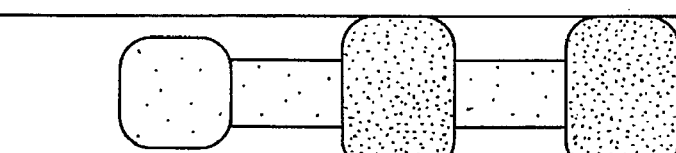
Figures 6, 74:
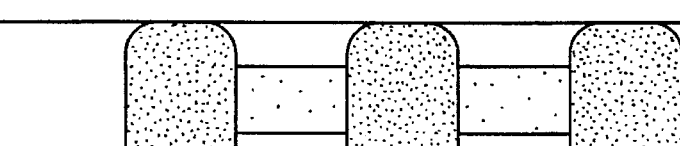
Figures 7, 74:
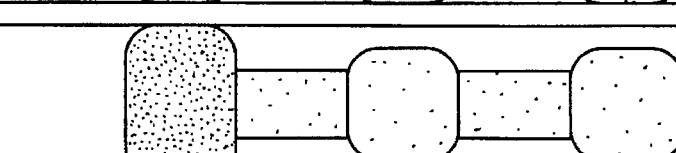

As shown in FIG. 5, in an alternate embodiment, two or more articulated arms 60 extend from the robot segment. The arms 60 are driven (like oars) in a controlled sequence to propel the robot. Balloons may or may not be used with the segments having the arms 60.

Figure 6:
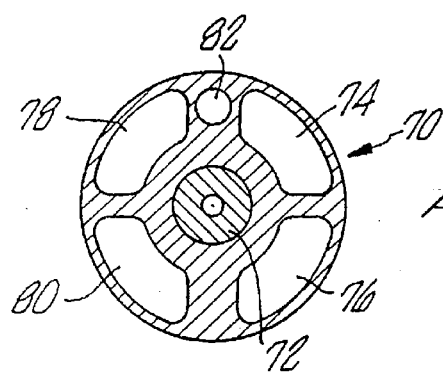
FIG. 6 is a partial section view of another embodiment of the present robot.

In another embodiment 70 shown in FIG. 6, a safety cable 72, of e.g., braided steel, Kevlar or carbon fibre extends centrally through the segments. Electrical power and control/communication lines 74, a gas supply line 76, a suction line 78, and an irrigation line 80 are spaced around the safety cable 72. A fiber optic cable 82 at the top of the robot delivers light to the front and/or back segments. In the event of a failure, the robot goes limp and can be withdrawn by pulling back on the safety cable.

Figure 7:
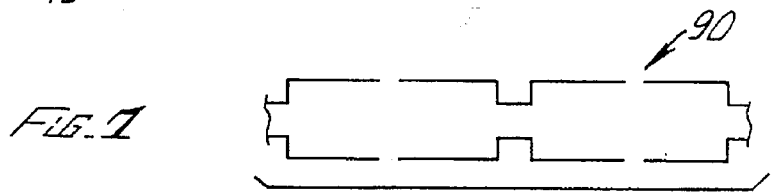
FIG. 7 is a side elevation view fragment of a sleeve component of the present robot.

FIG. 7 shows a cover or sleeve 90, preferably of plastic, which covers over and seals the robot segments. The sleeve 90 has openings for balloons or arms to extend through. The sections of the sleeve 90 between segments are highly flexible to allow the segments to freely move with respect to each other. The sleeve 90 may be removable, or a permanent part of the robot.

Figure 4:
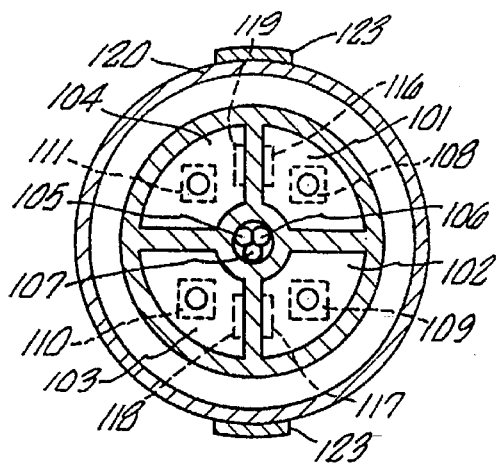
FIG. 4 is an end view of a segment of an alternative embodiment.
Figure 9:
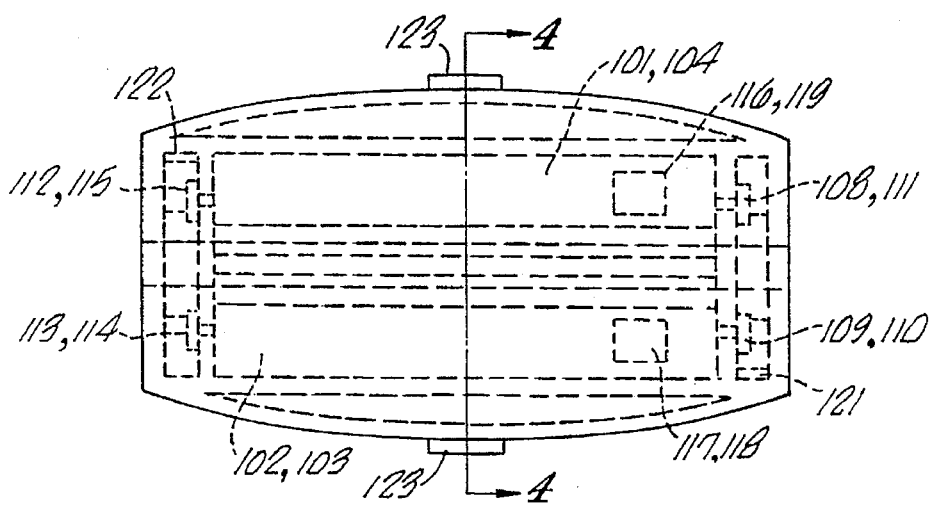
FIG. 9 is a side elevation view of the embodiment of FIG. 4.

As shown in FIGS. 4 and 9, an alternate embodiment of one robotic endoscope segment consists of four distinct inflatable sacs, 101, 102, 103, and 104. These sacs, which are comprised of an elastic material such as Latex, are circumferentially located around a central core. This core contains a high pressure compressed gas line 105, a low pressure or vacuum gas return line 106, and a control bus 107. Each sac is inflated or deflated by the action of valves 108–115. By controlling the relative pressure distribution in the sacs, using pressure sensors 116–119, the segment cannot only extend, as in the preferred embodiment, but also actively bend. This bending can be used to: actively control bending in parts of the intestine with tight radii of curvature and complicated shapes; position and orient the biopsy tool; implement concertina-like locomotion gaits; and assist in bracing of the robotic endoscope against the intestinal wall.

As in the previous embodiment, this alternate embodiment can also include a toroidal balloon 120 which is inflated or deflated by the action of valves 121 and 122. This balloon aids in the traction of the device by gripping the lumen wall. This embodiment can also include tactile sensors 123 on the exterior of the segment to control the reaction forces between the balloon 120 and the lumen wall. Of course, any number of sacs greater than or equal to three can be similarly used to effect the desired bending and extension of an individual segment.

Figures 1, 79:
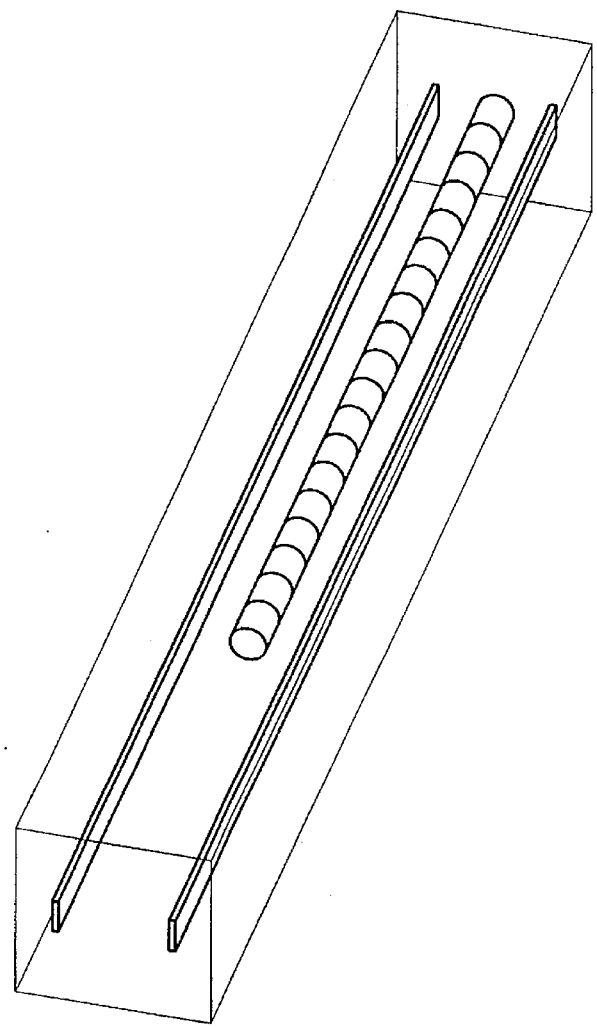
Figures 2, 79:
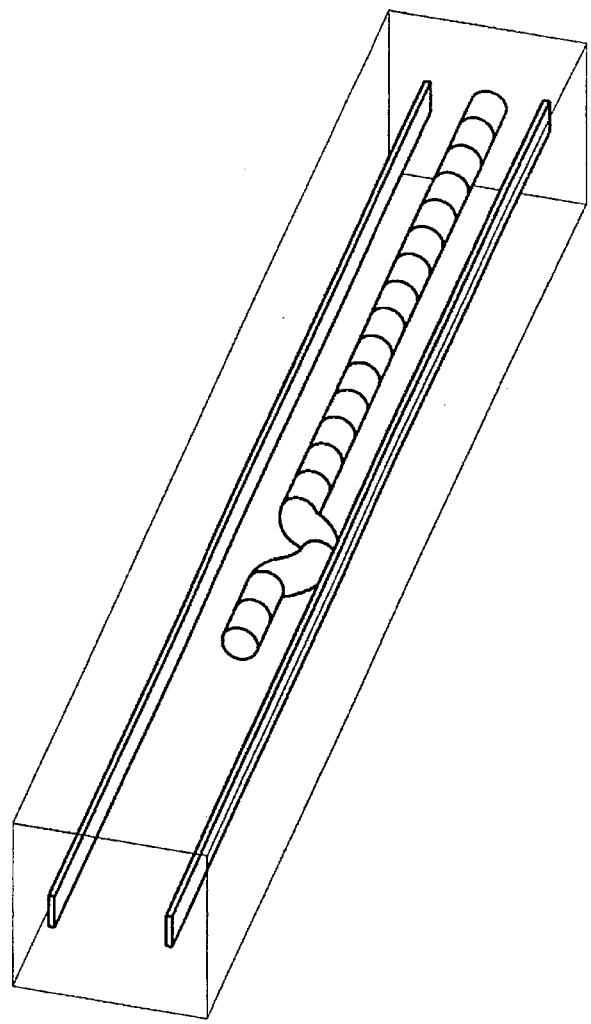
Figures 3, 79:
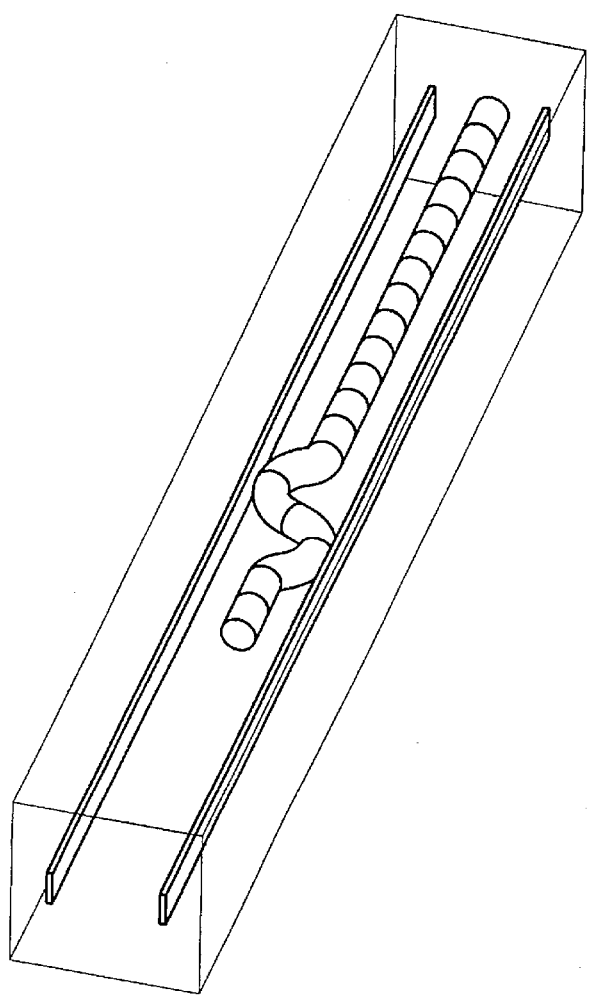
Figures 4, 79:
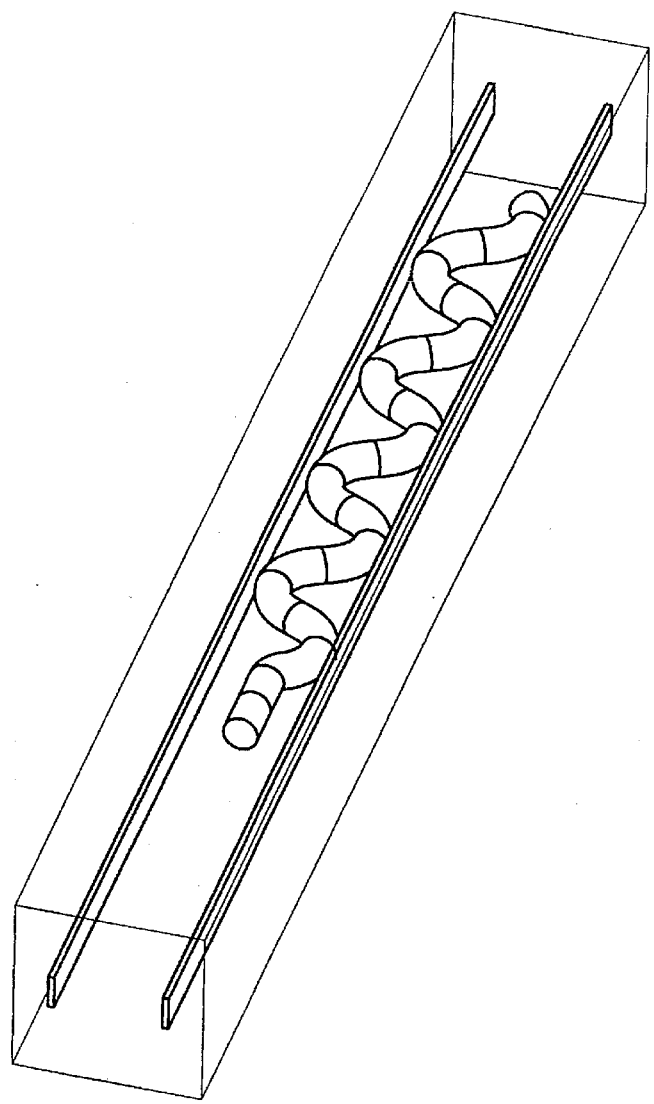
Figures 5, 79:
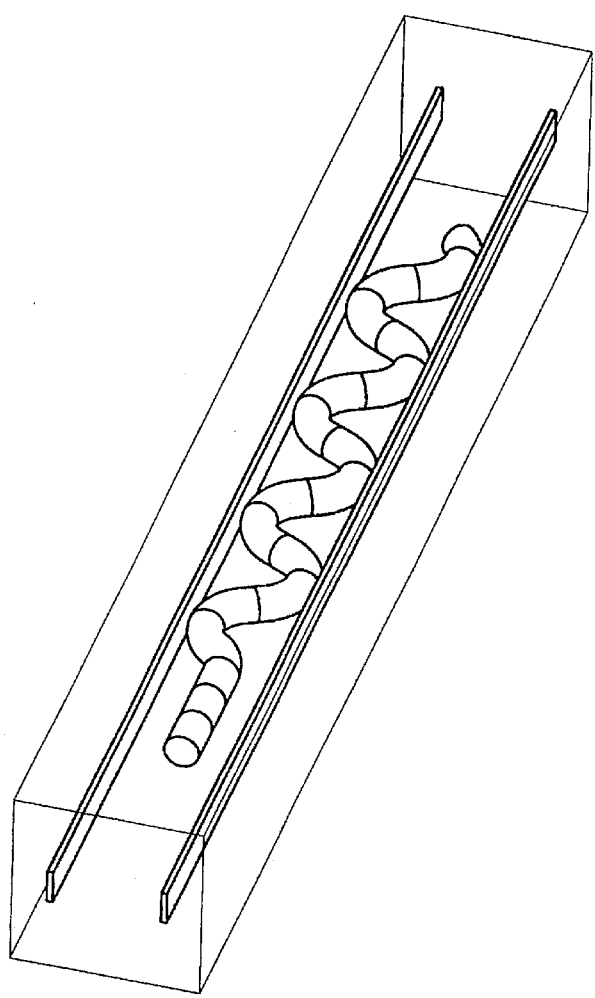
Figures 6, 79:
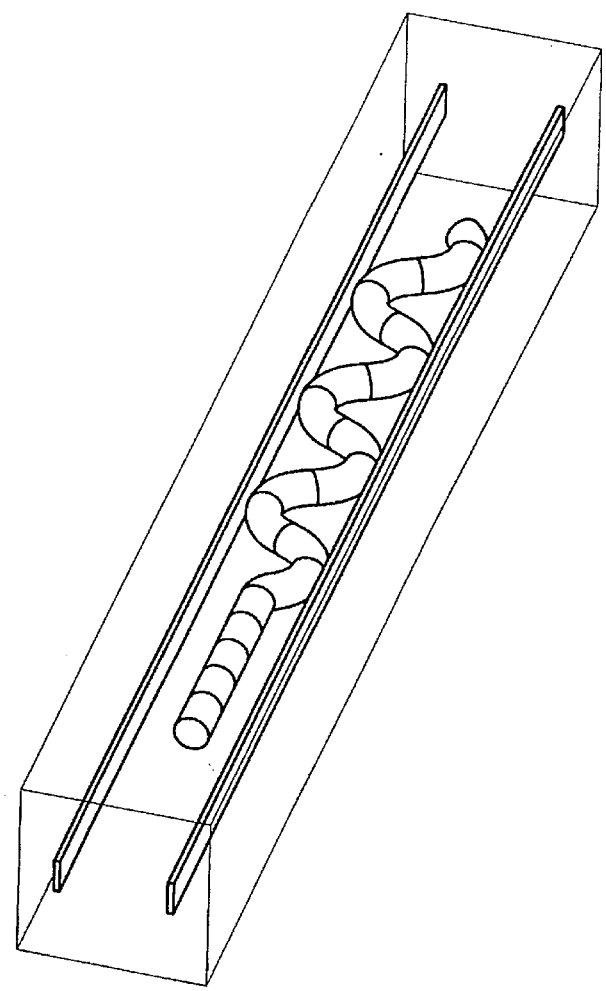
Figures 7, 79:
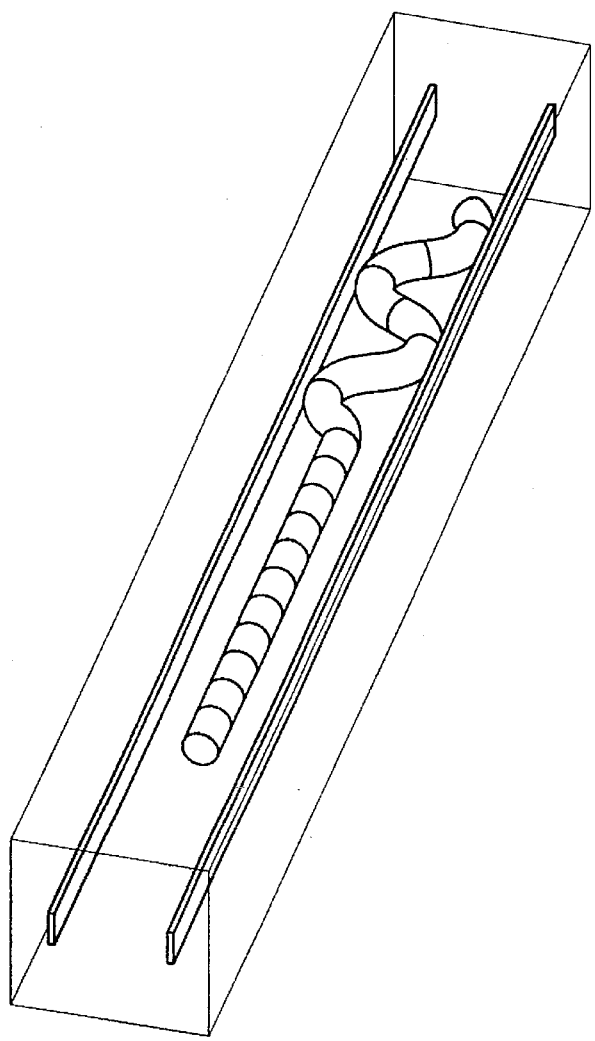
Figures 8, 79:
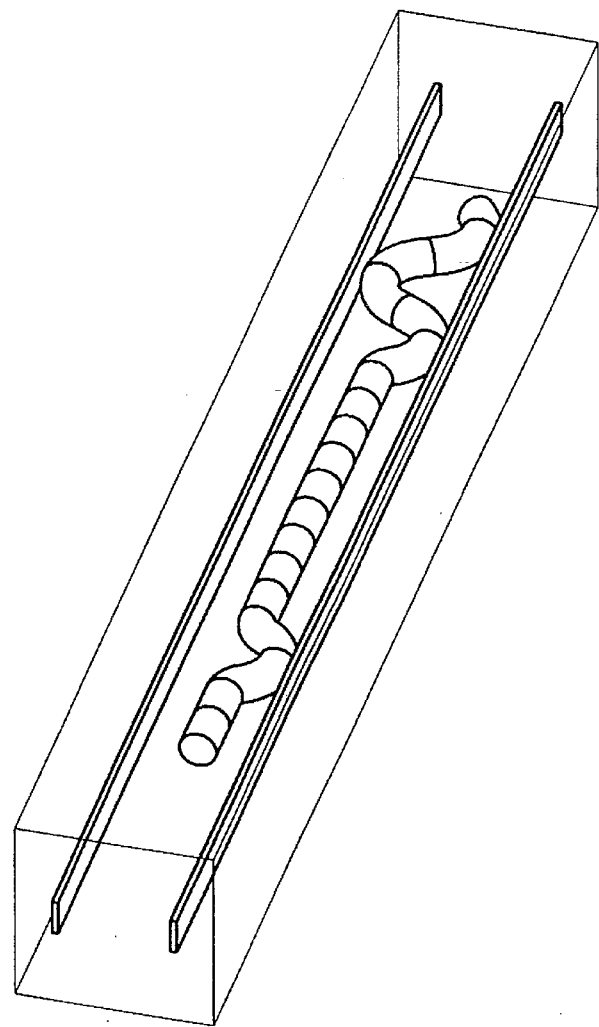
Figures 9, 79:
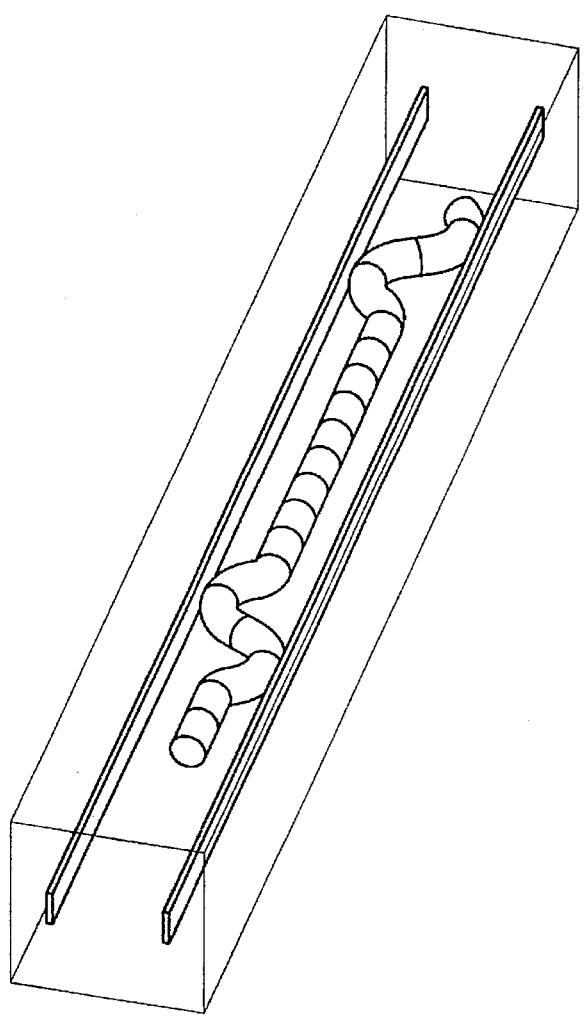
Figures 10, 79:
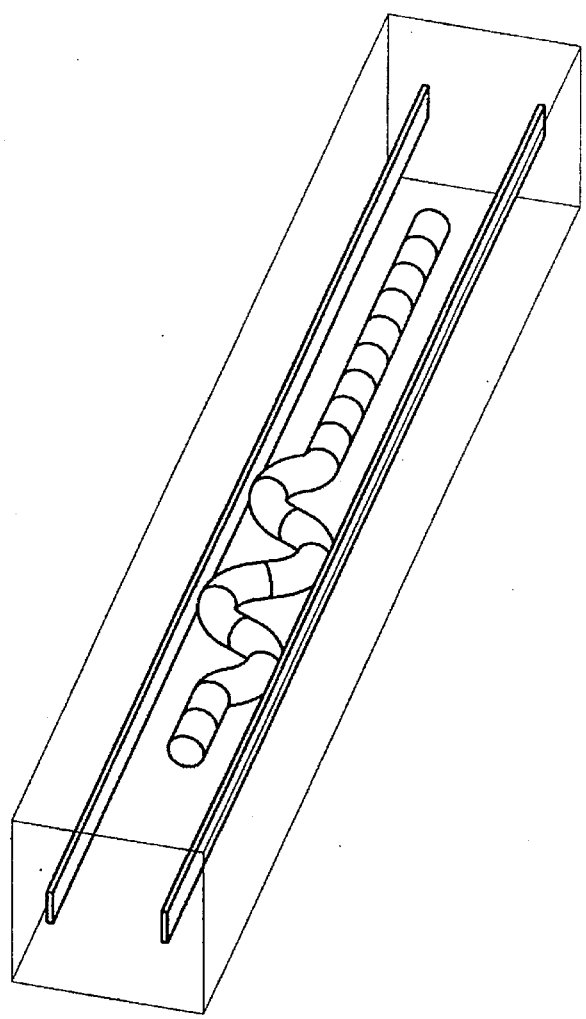
Figures 11, 79:
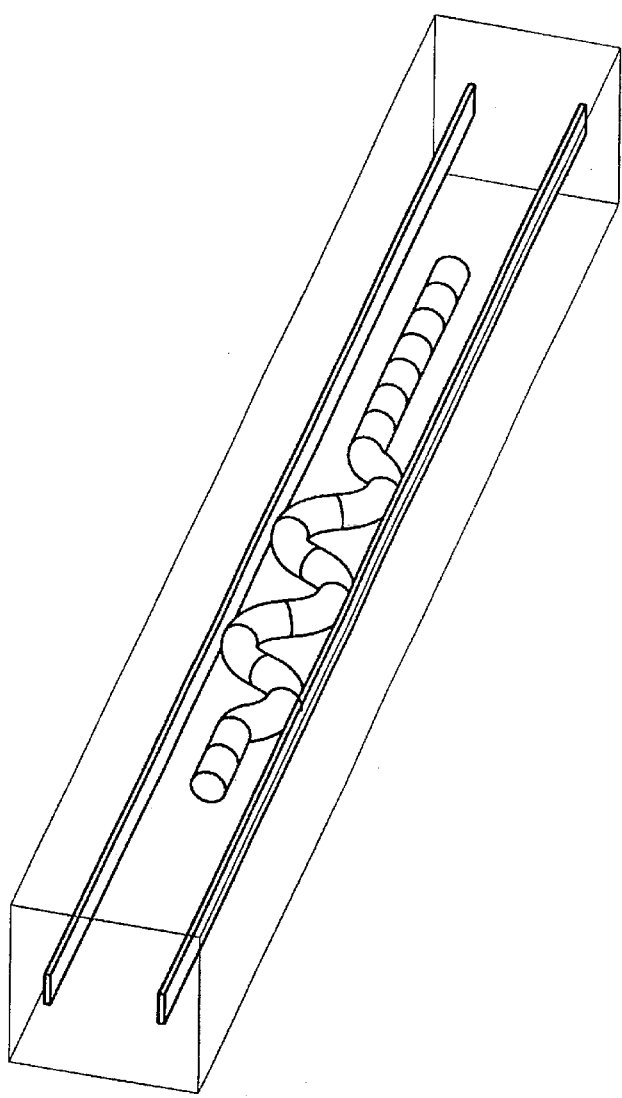
Figures 12, 79:
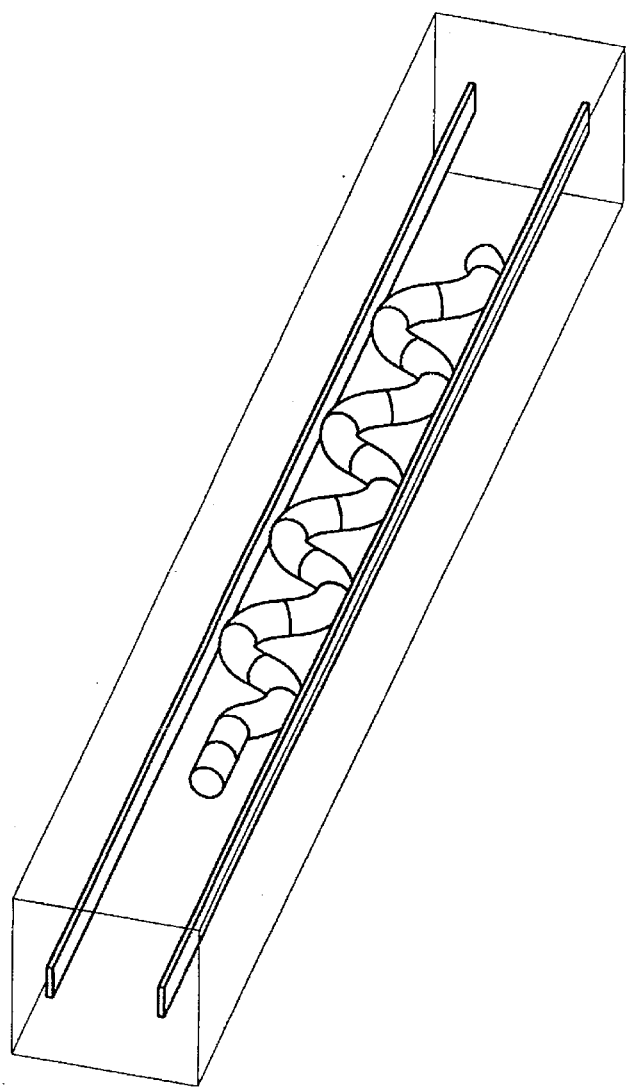

FIG. 8 shows a segment embodiment having bow wires 92 which can be bowed outwardly by an actuator 94, to brace against a lumen wall. Segments may have two or more bow wires radially spaced apart.

The propulsion, manipulation and steering aspects of the present invention may also be applied to catheters or other tubular devices. For example, the propulsion elements shown in FIGS. 4 and 9 may be made part of or attached around a catheter. In addition, other devices having a series of segments, not necessarily only endoscopes, may include the present designs to achieve the propulsion described above. Indeed, the term "endoscope" as used herein is intended to be generic to endoscopes, catheters and other elongate medical devices.

The various possible embodiments of the present robotic endoscope employ mechanisms which can be described loosely as "grippers" and "deformers." The primary purpose of the grippers, or traction devices, is to provide traction against the lumen wall. The gripper or traction modules grasp the inside surfaces of the encompassing lumen by locally increasing the effective diameter of the gripper module. The gripper modules should allow the endoscope to "softly" grasp the inner linings of the lumen so as to minimize any potential injury to its possibly fragile tissues. The primary purpose of a deformer is to locally change or distort the shape of the endoscope. These changes represent bending and stretching actions, which may be controlled by a computer. The endoscope preferably includes multiple gripper and deformer modules along its length. The modules themselves have many possible designs.

Effective locomotion of the endoscope through lumens which exhibit changing geometric or material characteristics along their length (e.g. varying cross-sectional diameter) may require changes of maneuvering sequences. A particular embodiment of the invention may be limited to a subset of all the possible maneuvers detailed below since different gripper and deformer mechanisms would tend to be better suited to different maneuvering sequences. In general, these maneuvers may be categorized as inchworm-like, concertina-like, and maneuvers which combine the features of inchworm and concertina movements.

Traction Modules

Various mechanisms will produce a gripping effect. Although the preferred embodiments utilize different types of balloons for this purpose, other mechanical equivalents could also be employed. "Oars," "bow wires," "mollies," and four bar kinematic linkages all represent possible embodiments for these modules.

Figure 10:
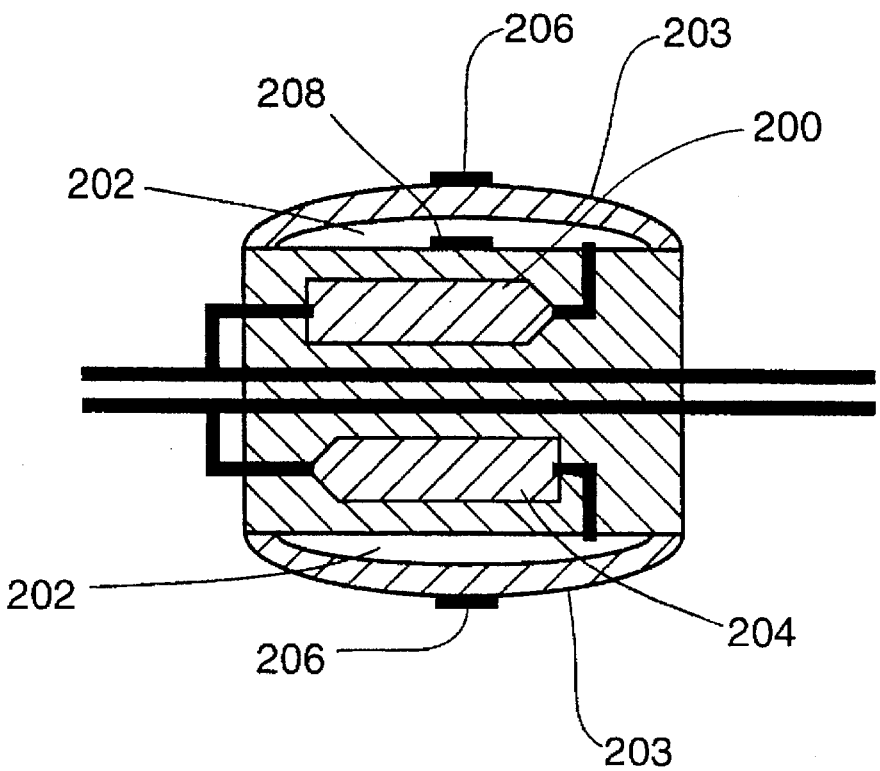
FIG. 10 is a longitudinal section view of a traction module for inchworm type locomotion.
Figure 11:
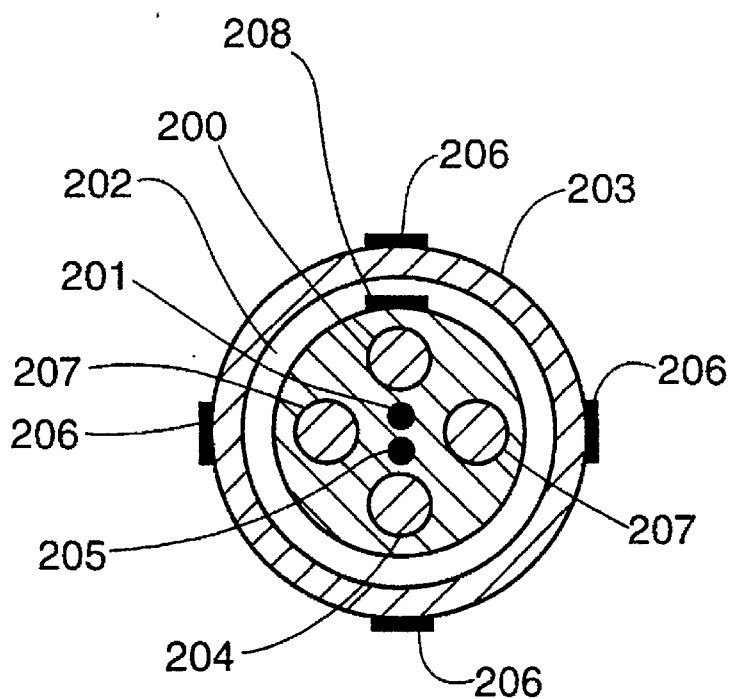
FIG. 11 is a lateral section view thereof.

FIGS. 10 and 11 show an embodiment somewhat similar to FIG. 3, by opening the high pressure servovalve 200, fluid or gas from the high pressure source line 201 is allowed to enter the inner chamber 202 thereby distending the balloon surface 203. Once the balloon is sufficiently inflated, the high pressure servovalve 200 is closed.

Tactile sensors 206, similar to sensors 50, may be applied to the outer surface of the balloon 203, to measure the forces that the balloon device applies to the lumen walls. Although shown as discrete elements, these sensors 206 may take the form of a single tactile skin completely surrounding the balloon surface 203. Additionally, special materials may be applied to the surface of the balloon 203 to enhance the traction against the slippery inner walls of the lumen. Such traction aids may include: elastomeric materials such as velcro, silicone, elastomers, PCV, PTFE, and polyethylene, and/or texturing such as rib-like features, nubs, and sponge-like surfacing. For the same purpose, certain hydrophilic and hydrophobic materials on the surface of the balloon 203 may be helpful. An internal pressure sensor 208 may be included to measure the internal pressures within the balloon. When traction against the lumen is no longer desired, the low pressure servovalve 204 is opened to allow the fluid or gas within the inner chamber 202 to be evacuated into the low pressure source line 205. Once the balloon is deflated, the low pressure servovalve 204 is closed. These 2-way, normally closed servovalves 200 and 204 allow the module to remain in any desired degree of inflation without expending any electrical energy. This may be necessary if the robotic endoscope is to receive its electrical power from batteries.

The two 2-way servovalves 200 and 204 may be replaced by a single 3-way servovalve. Two additional 2-way servovalves 207 may be incorporated into the module to allow inflation and deflation of an adjacent fluid powered extensor or bender module. Likewise, the two servovalves 207 may be replaced by a single 3-way valve.

A second family of traction/gripper modules is shown in FIGS. 12–17. In these embodiments, two or more arms or "oars" are hinged to extend away from the central body 210 of the module. Each arm, such as arm 211 may have a special end 212 that is surfaced with traction aids as described above. The special ends may contain tactile sensors to measure the forces imposed by the robotic endoscope on the surrounding lumen. The sensors connect to the electronic bus, such as 52 or 107, associated with the locomotion control. These arms may be actuated by a variety of ways, including pneumatics, hydraulics, electromagnetic actuation, shape memory alloys, magnetostrictive materials, electrostrictive materials, piezoelectric materials, etc. Sensors to measure the extent to which the arms are displaced outwardly may be incorporated in their joints 213.

A sheath 214 surrounding the module may be provided to contain the entire mechanism as shown in FIGS. 18–23. The sheath shields the module from the foreign bodies/liquids which exist in the gastrointestinal tract or elsewhere in the body. A discrete tactile sensor or distributed tactile sensor skin may also be applied to the sheath to measure the forces imposed on the lumen walls by the endoscope. The sheath may also have traction aids.

In another embodiment as shown in FIGS. 24–27, the effective diameter of the module is increased when semicircular cylindrical shells 217 are displaced from the central body 215 by the action of pairs of links 216. Because the links 216 are of equal length, the semicircular cylindrical shells are always parallel to the central body 215. The cylindrical shells 217 may be displaced by a variety of mechanical means, e.g., pneumatic actuators. The outer surface of the semicircular cylinders 217 may contain sensors to measure the contact loads imposed by the module on the surrounding lumen. These surfaces may also be covered with traction aids. As shown in FIGS. 29–33, the traction module may include an outer sheath 218 to protect the module from foreign bodies/fluids as well as providing surfaces for traction aids and tactile sensors.

Figure 28:
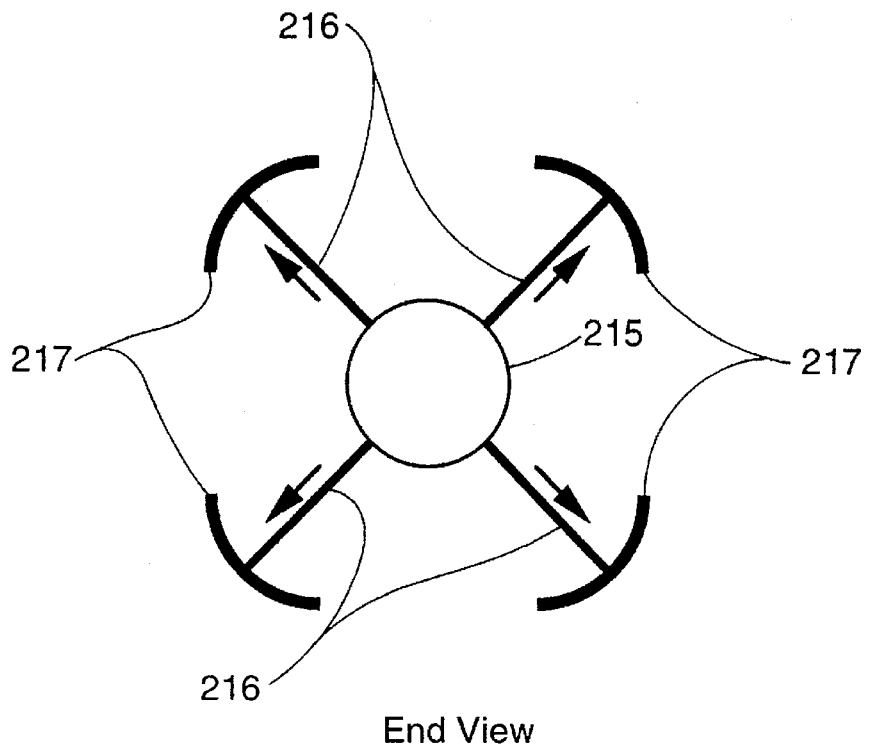
FIG. 28 is an end view of an alternative traction embodiment module having multiple actuated cylindrical shells.
Figure 33:
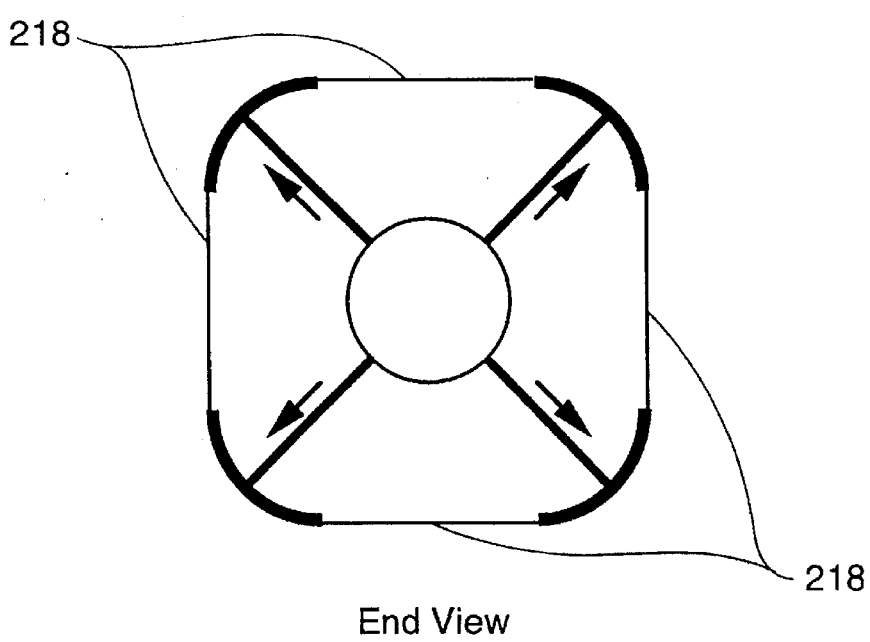
FIG. 33 is a schematically illustrated end view of traction module, similar to the module of FIG. 28, and further including a sheath.
Figure 29:
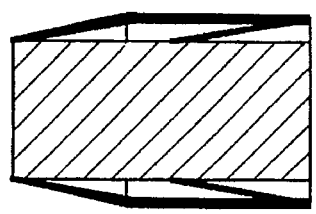
FIG. 29 is a schematically illustrated side elevation view of an alternative traction module embodiment in the contracted position, similar to the module of FIG. 24, and further including a sheath.
Figure 30:
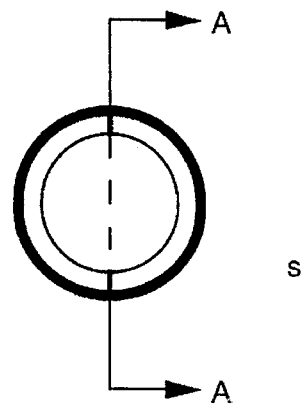
FIG. 30 is an end view thereof.
Figure 31:
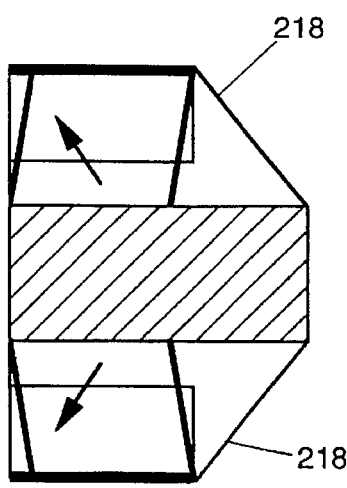
FIGS. 31 and 32 show the traction module of FIGS. 29 and 30 in the extended position.
Figure 32:
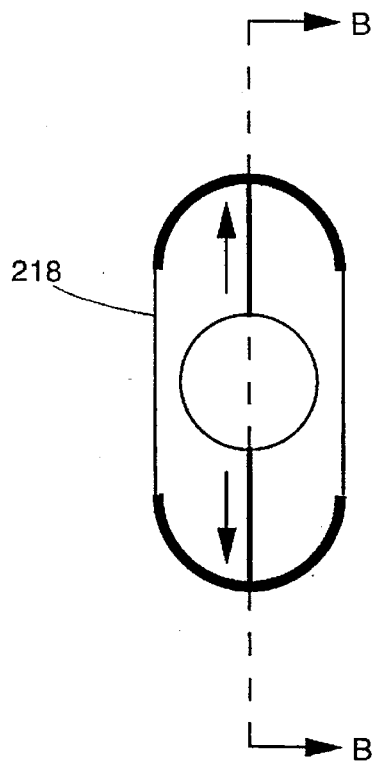
Figure 34:
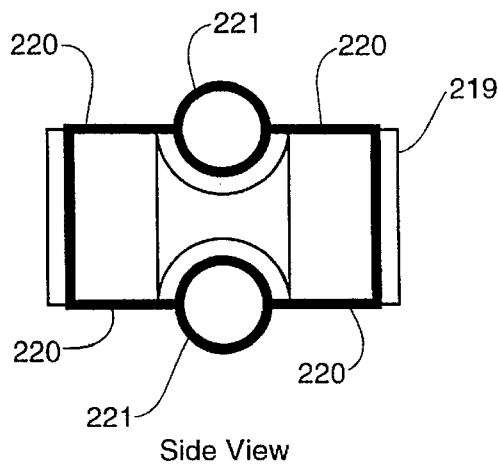
FIG. 34 is a schematically illustrated side elevation view of another traction module embodiment, in the contracted position, wherein the effective diameter of the module is increased by a reduction of the distance between the base of the links.
Figure 35:
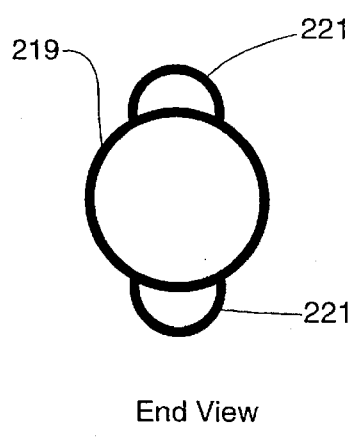
FIG. 35 is an end view thereof.
Figure 36:
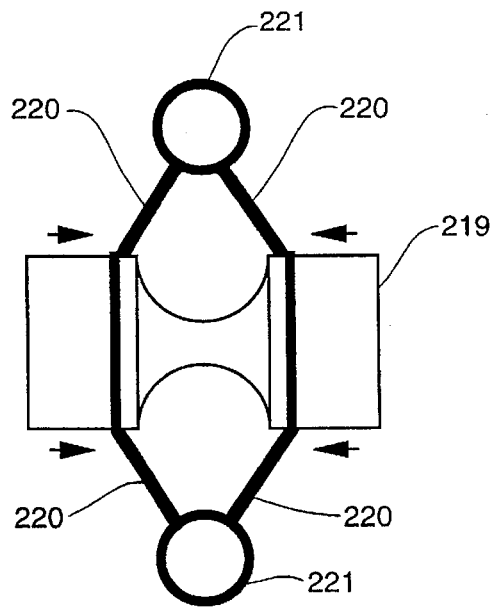
FIGS. 36 and 37 show the traction module of FIGS. 34 and 35 in the expanded position.
Figure 37:
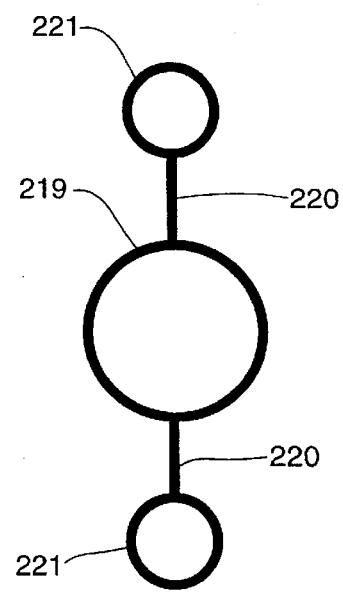
Figure 39:
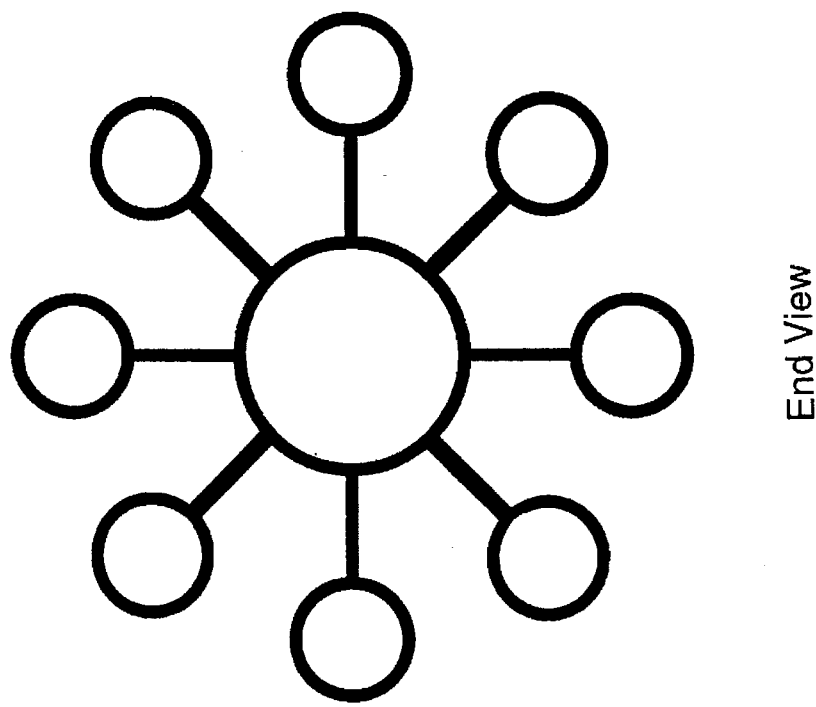
FIGS. 38 and 39 are schematically illustrated end views of alternative traction module embodiments.
Figure 38:
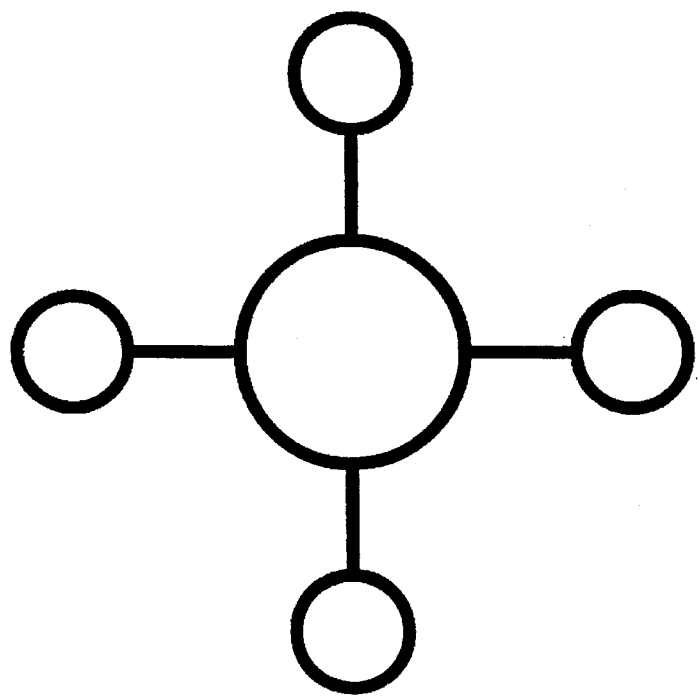
Figure 40:
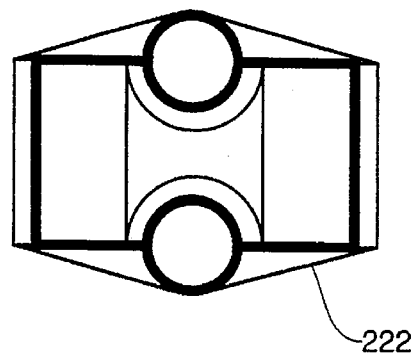
FIG. 40 is a schematically illustrated side elevation view of an alternative traction module embodiment, in the contracted position, similar to the embodiment of FIG. 34, and further including a sheath.
Figure 41:
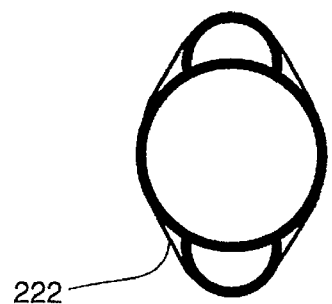
FIG. 41 is an end view thereof.
Figure 42:
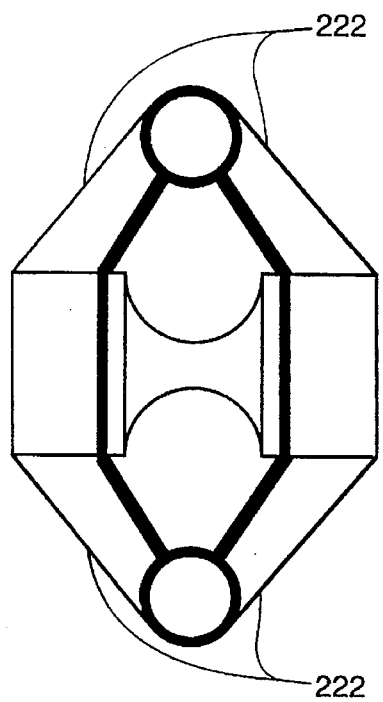
FIGS. 42 and 43 show the traction module of FIGS. 40 and 41 in the expanded position.
Figure 43:
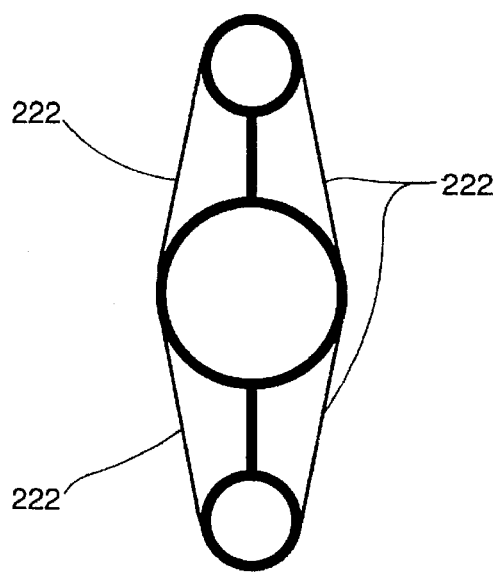
Figure 45:
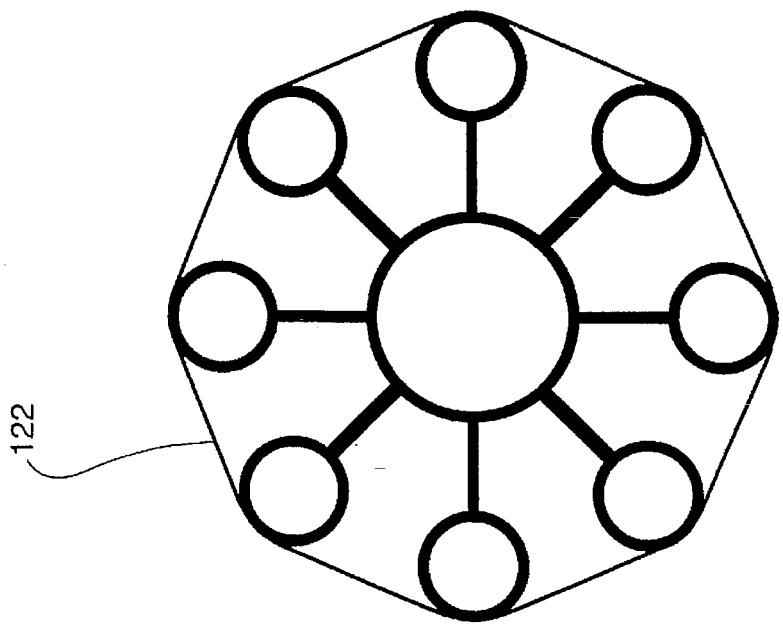
FIGS. 44 and 45 show embodiments similar to the embodiments of FIGS. 38 and 39, and further including a sheath.
Figure 44:
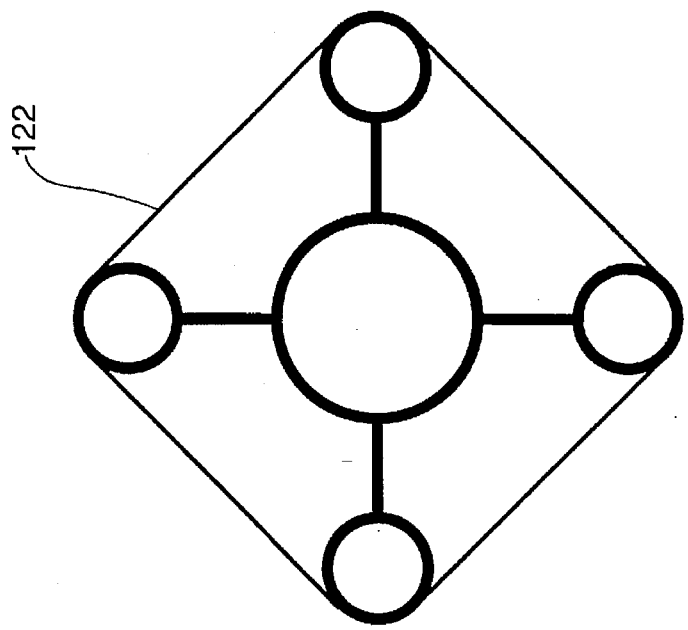
Figure 46:
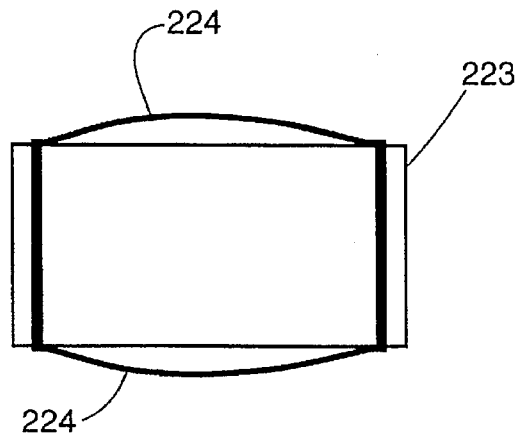
FIG. 46 is a schematically illustrated side elevation view of another traction module, in the contracted position, similar to the embodiment of FIG. 8.
Figure 47:
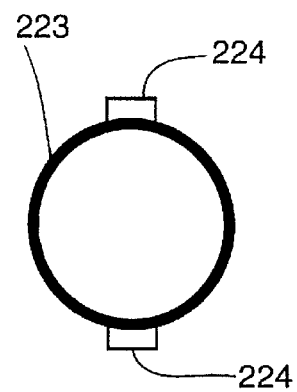
FIG. 47 is an end view thereof.
Figure 48:
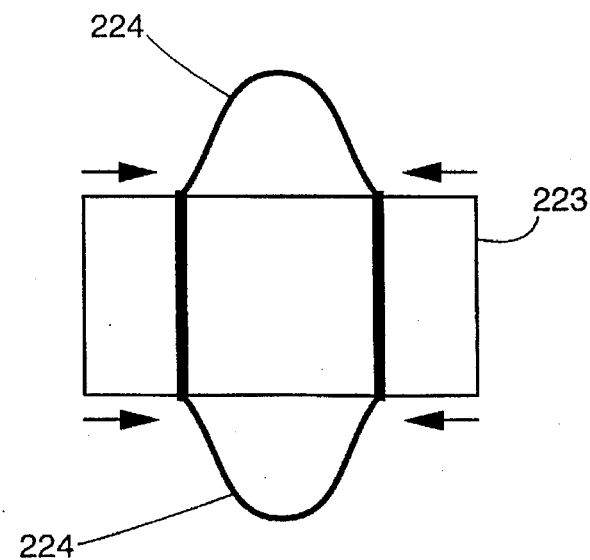
FIGS. 48 and 49 show the traction module of FIGS. 46 and 47 in the expanded condition.
Figure 49:
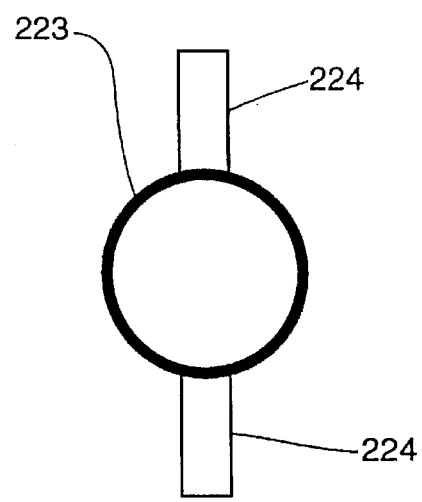

FIG. 28 shows an embodiment including multiple actuated cylindrical shells around the circumference of the central body, and linkages around the circumference of the traction module.

Another embodiment of a traction module shown in FIGS. 34–39 is similar to the "oar" embodiments. In these designs, the effective diameter of the module is increased by a reduction of the distance between the bases of the links 220 along the module axis. As the bases of the links 220 approach each other, each hinge and contact "foot" 221 moves laterally away from the module centerline. As in the case with the traction module of FIGS. 12, this embodiment can utilize at least two such linkages around the circumference of the module. Each contact foot 221 can be covered with the traction aids described above. A sheath covering 222 may also be used over the module as shown in FIGS. 40–45. The actuation technology (pneumatics, shape memory alloys, electromagnetism, etc.) of these mechanisms will be chosen in accordance with necessary patient safety considerations as well as desired performance goals.

Figure 50:
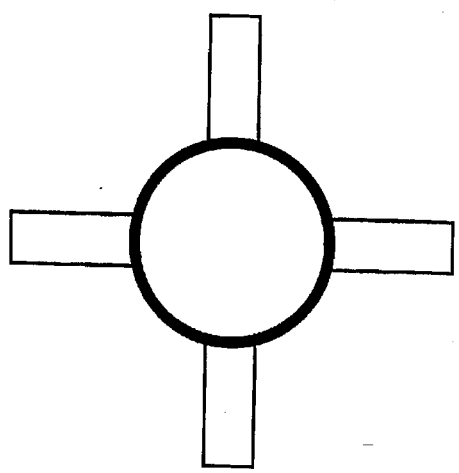
FIGS. 50 and 51 are schematically illustrated end views of alternative traction module embodiments, similar to the embodiment of FIGS. 46–49.
Figure 51:
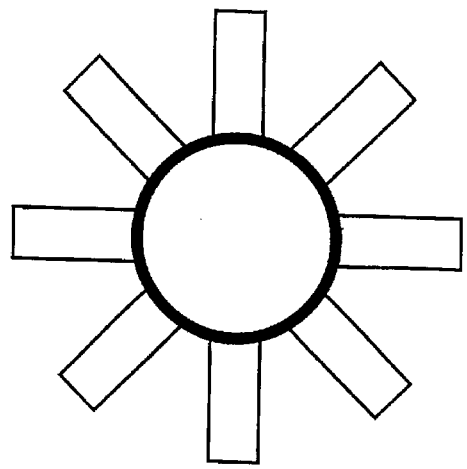
Figure 52:
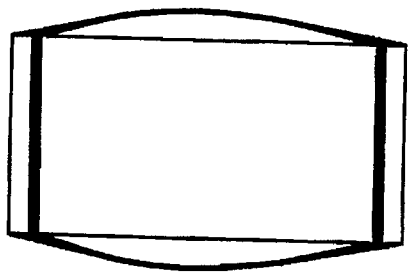
FIG. 52 is a schematically illustrated side elevation view of a traction module, in a contracted position, similar to the embodiment of FIGS. 46–49, and further including a sheath.
Figure 53:
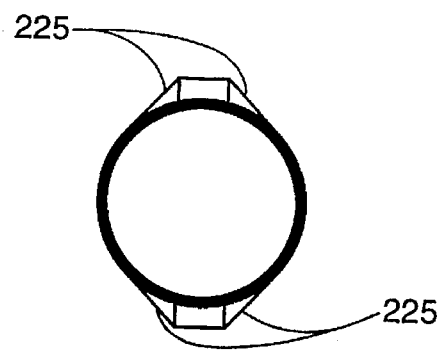
FIG. 53 is an end view thereof.
Figure 54:
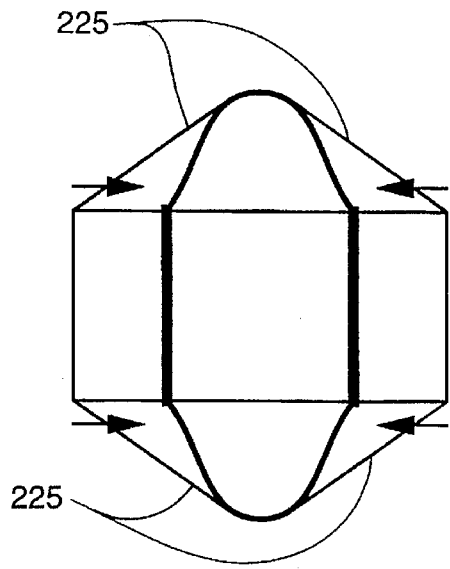
FIGS. 54 and 55 show the traction module of FIGS. 52 and 53 in the expanded position.
Figure 55:
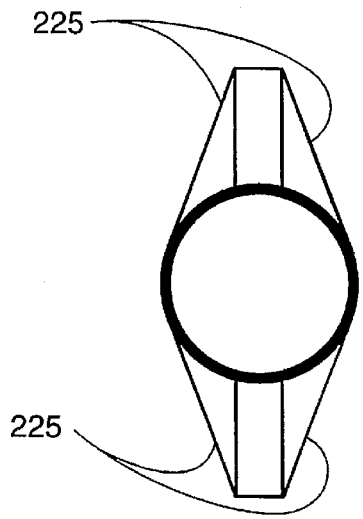
Figure 56:
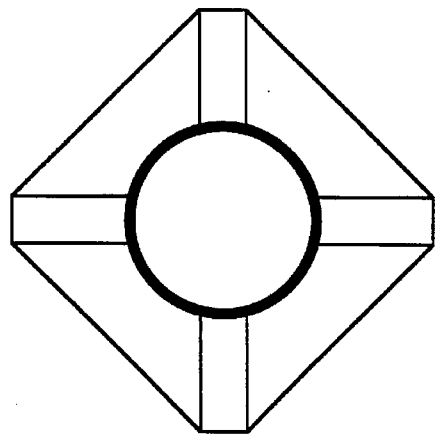
FIGS. 56 and 57 are end views of alternative traction module embodiments, similar to the embodiments of FIGS. 50 and 51, and further including a sheath.
Figure 57:
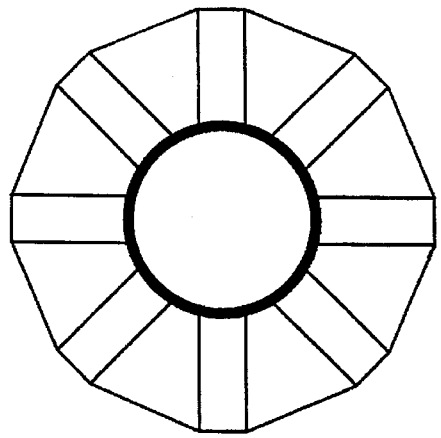

FIGS. 46–51 show a design similar to FIG. 8 wherein when the lateral expansion is desired, actuators pull the bases of the "bow wires" 224 closer along the surface of the central body 223. This action causes the "bow wires" 224 to buckle away from the module centerline. The bow wires 224 have cross-sections which cause them to bow radially away from the module centerline. The outer surfaces of the bow wires 224 may incorporate sensors to measure the contact loading onto the lumen. In addition, they may also have coverings that help produce traction. FIGS. 50 and 51 show end views of bow wire embodiments which utilize four and eight bow wires. Other numbers of bow wires can be used.

The embodiments of FIGS. 46–51 may also include a protective sheath 225, as shown in FIGS. 52–57. The embodiments of these traction modules may have a control bus (such as bus 52 in FIG. 1), a safety cable (such as cable 72 of FIG. 6), communications line (such as lines 74 of FIG. 6), and compressed gas supply lines (such as lines 76 of FIG. 6). These features are omitted in FIGS. 12–57, for clarity of illustration.

Extensor Modules

In a robotic endoscope which propels itself by inchworm type movements, extensor modules are interspersed between the traction modules. These extensor modules provide the local axial expansion and contraction required for inchworm type movement. Since lumens in human or animal physiology are often substantially curved along their length, the extensor modules must be able to bend laterally. In many applications passive bending compliance would be sufficient to allow the robot to negotiate a curved lumen. However, actively controlled bending of the extensor modules may be necessary for certain applications. Various extensor module embodiments are possible, including mechanisms based on bellows, air/hydraulic cylinders, solenoids, voice coil motors, electric motors with lead screw transmissions, etc., which provide changes in the axial length of the module.

Figure 60:
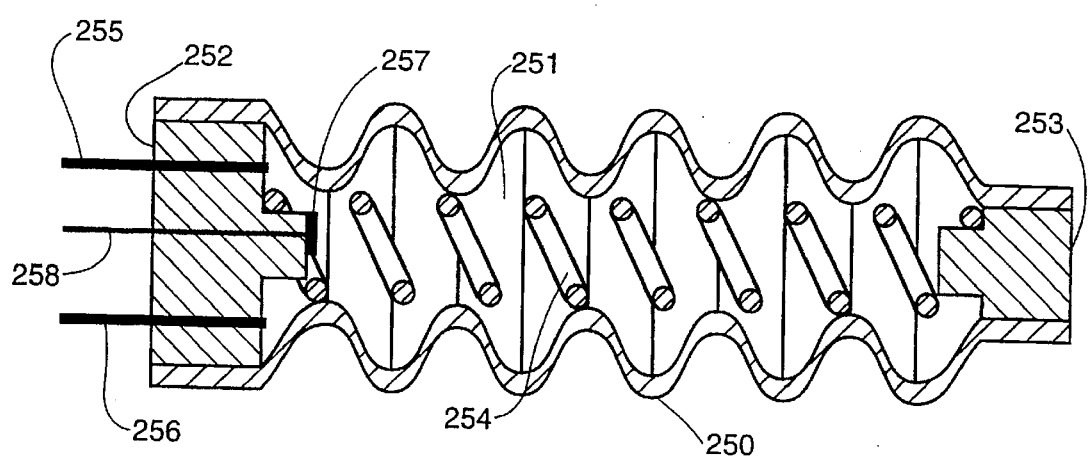
FIG. 60 is a schematically illustrated section view of a bellows type extensor module.
Figure 61:
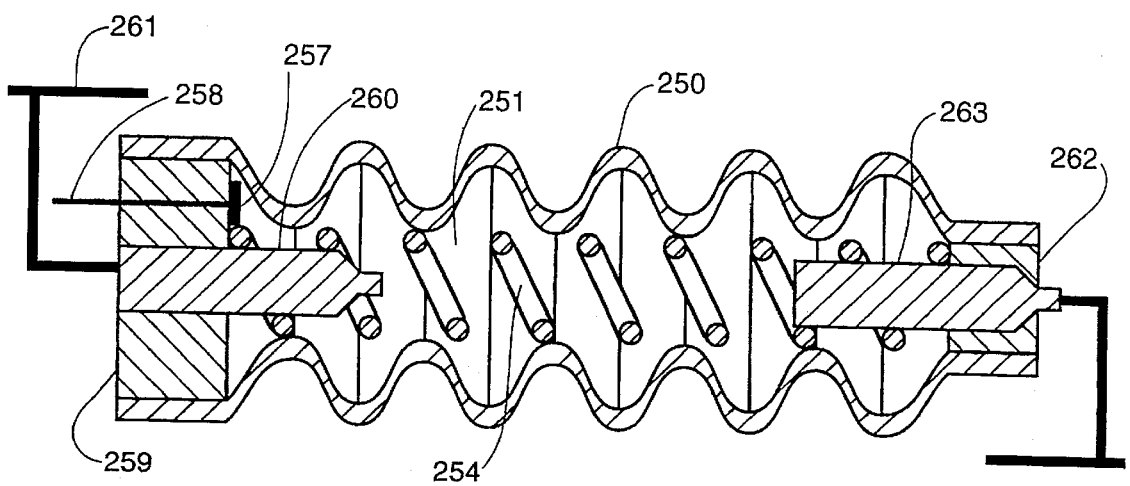
FIG. 61 is a schematically illustrated section view of an alternative design bellows type extensor module wherein the servovalves are within the module.

FIGS. 58–61 show preferred embodiments of passive bending extensor modules. FIG. 60 is a section view of a bellows type extensor module embodiment in which the servovalves of the actuator are contained in an adjacent traction module, such as the servovalves 207 of FIG. 10. FIG. 61 is a section view of a bellows type extensor module embodiment in which the servovalves 260 and 263 of the actuator are installed directly within the module. In both embodiments, a compliant bellows 250 forms the outer surface of the module. These embodiments are characterized by their longitudinal expansion under the action of fluid or gas injected and removed from the central chamber 251. Their structure allows them to bend passively under lateral loading.

Turning now in detail to FIG. 60, at each end of the bellows 250 are plugs 252 and 253 which seal the module while also providing points of attachment to the adjacent modules. Between these plugs 252 and 253 is a spring 254 which provides the desired lateral and longitudinal stiffness. The spring 254 also prevents the bellows from contracting laterally instead of longitudinally when a partial vacuum is applied to the inside of the bellows. One of the plugs 252 may contain a port 255 connected to the high pressure servovalve within an adjacent traction module, e.g. 207 of FIG. 10, which is used to inflate the extensor module. This plug 252 may also contain the port connection 256 to the low pressure servovalve within an adjacent traction module which is used to deflate the extensor module. Either or both of these ports 255 and 256 may be located within the other plug 253. A pressure sensor 257 and wiring 258 may attached to the plug 252 which is used by the control electronics of the robot to determine when the inflation and deflation valves are to be closed. The sensor may also be installed in the other plug 253.

A modification of this extensor module embodiment is shown in FIG. 61 wherein the inflation and deflation servovalves 260 and 263 are located within the module. In this design, the function of the components of the extensor module is fundamentally the same as that of the embodiment of FIG. 60 except for the actions of the end plugs 259 and 262 which now house the servovalves 260 and 263 (in contrast to plugs 252 and 253 of FIG. 60). In FIG. 61, the high pressure source line 261 is connected to the high pressure servovalve 260, located within the left end plug 259. When the high pressure servovalve 260 is opened, fluid from the high pressure source line 261 flows into the extensor module and extends it. The high pressure servovalve 260 is closed once the extensor module has reached its desired length. This design allows the extensor module to remain at any desired configuration without expending any energy as the 2-way servovalves 260 and 263 are of the normally closed variety. Alternatively, the 2-way servovalves 260 and 263 may be replaced by a single 3-way valve if desired. The remaining components shown in FIG. 61 may be the same as in FIG. 60.

Figure 62:
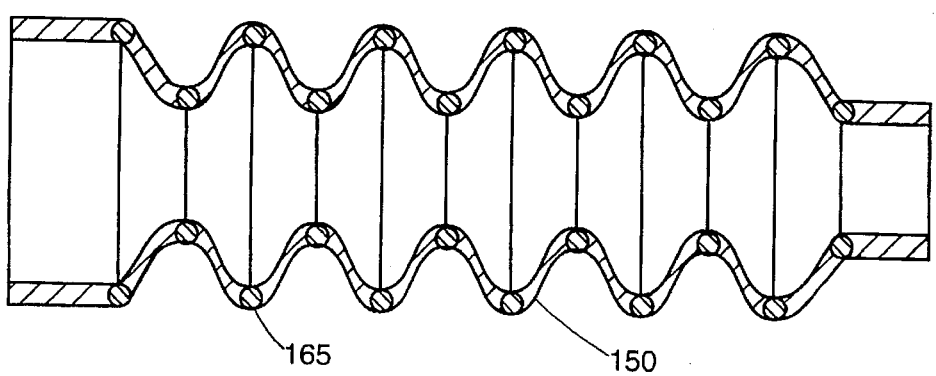
FIG. 62 is a schematically illustrated section view of an alternative bellows type extensor module embodiment having metallic wire or other composite fibers for reinforcing the bellows.

FIG. 62 shows a modification of the bellows type extensor module embodiments which uses metallic wire or other composite fibers 265 to reinforce the bellows 250, thereby enhancing its strength and stiffness. The increased stiffness of the reinforced bellows may obviate the need of the internal spring 254 of FIGS. 60 and 61. This feature may be used in any of the bellows embodiments.

Figure 63:
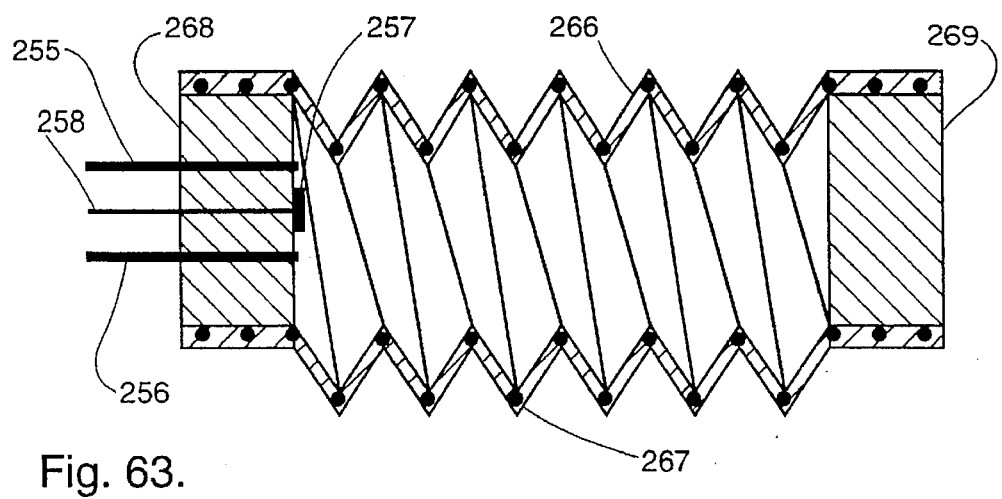
FIG. 63 is a schematically illustrated section view of a bellows type extensor module, similar to the embodiment of FIG. 60, and having a helical bellows.
Figure 64:
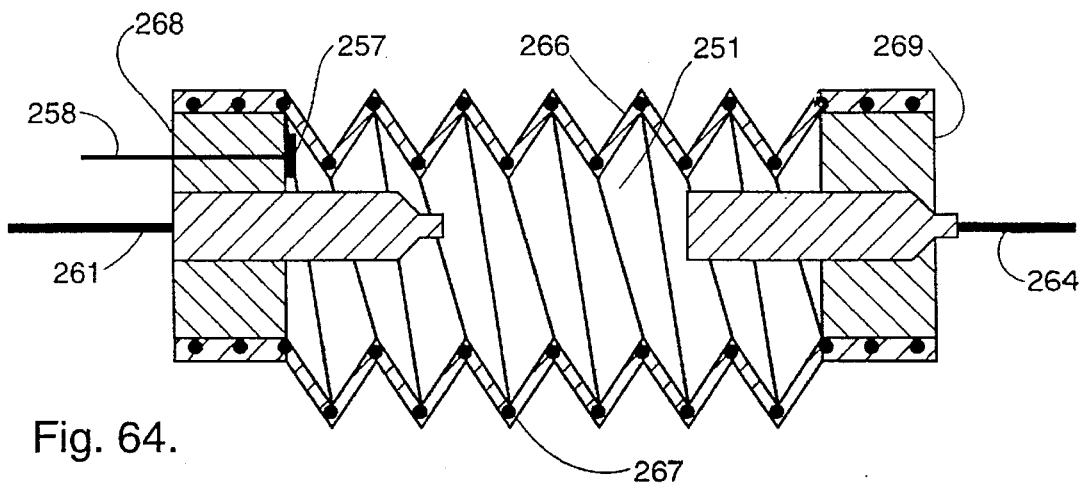
FIG. 64 is a schematically illustrated section view of an alternative bellows type extensor module embodiment, similar to the embodiment of FIG. 60, and having modified end plugs.

FIG. 63 illustrates a modification of the embodiment of FIG. 60 and uses a helically designed bellows 266 in place of the standard bellows 250 in FIG. 60. This helical bellows 266 may incorporate a substructure 267 made of metal wire or other stiffening or strengthening material, to aid or replace the action of the spring 254 in the embodiment shown in FIG. 60. The plugs 268 and 269 are redesigned as necessary to function in the same capacity as 252 and 253 of FIG. 60. A similar modification can be made to the embodiment shown in FIG. 61, as shown in FIG. 64.

Figure 65:
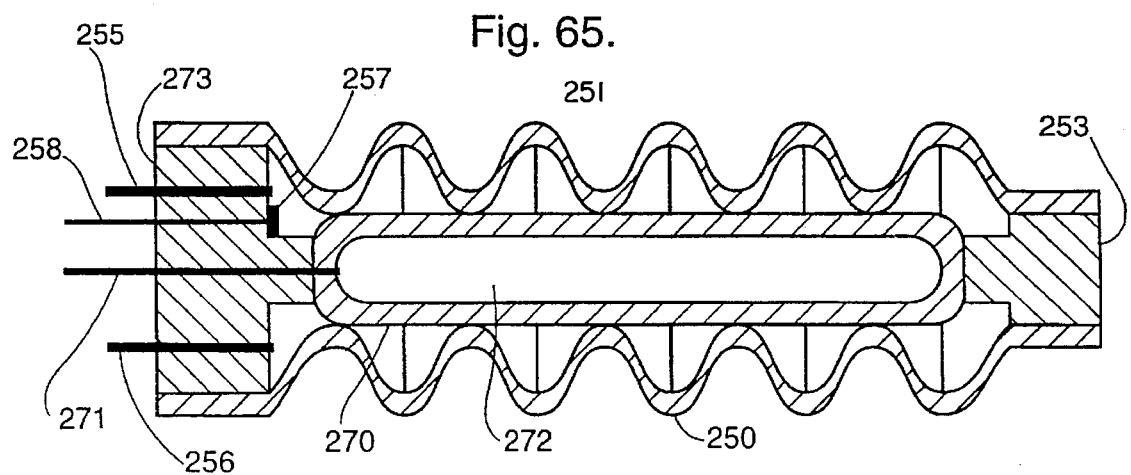
FIG. 65 is a schematically illustrated section view of an alternative bellows type extensor module embodiment, similar to the embodiment of FIG. 60, and including an air spring instead of a standard mechanical spring.

FIG. 65 illustrates an embodiment which uses an air spring 270 in place of the standard spring 254 in the embodiment shown in FIG. 60. This air spring 270 changes its lateral and longitudinal stiffness as a function of the pressure of the fluid within its central chamber 272. This internal pressure can be changed by the flow of fluid through the port 271. In this embodiment, the end plug 252 is replaced with a modified version 273.

Other extensor module embodiments could be produced by using a variety of mechanisms. The desired, laterally compliant, mechanical extension action can be generated by any of the following: (a) an air/hydraulic cylinder with a joint attached to the end of the piston rod (see FIG. 3); (b) a lead screw mechanism attached to an electric motor; (c) a linear piezoelectric inchworm or ultrasonic motor mechanism with a jointed actuator rod to provide the necessary lateral compliance, and (d) a solenoid driven jointed rod mechanism. Other designs and equivalents are also possible and will be apparent to those skilled in the art.

Bender Modules

Figure 66:
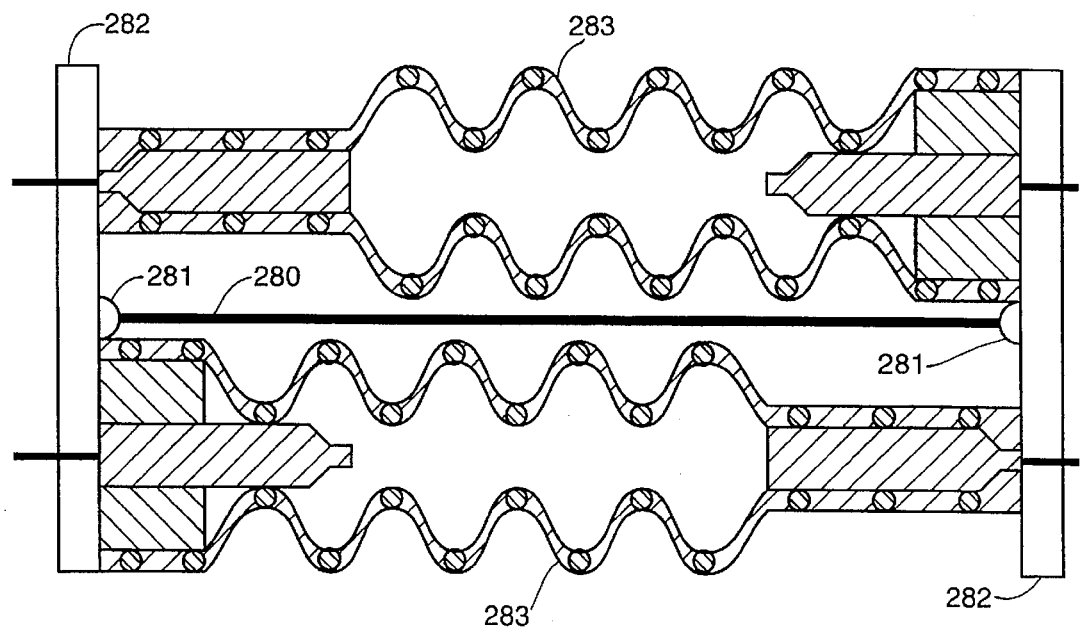
FIG. 66 is a schematically illustrated section view of a bender module.

Modules which can provide active bending are required for the endoscope to undergo concertina type locomotion. In addition, such modules may be used to steer the lead segment of the robotic endoscope to improve its diagnostic capability and to enhance its ability to negotiate curved lumens. FIG. 66 shows a bender module embodiment having a central link 280 attached through joints 281 to two end plates 282. Around this link are two or more linear actuators, here shown as fluid power bellows actuators 283. The action of these linear actuators causes the end plates 282 to change their angular orientation relative to one another. Many other linear actuation technologies could be employed to replace the action of the bellows actuator 283, such as shape memory alloy wires, solenoid/voice coil actuators, etc.

Combination Modules

Modules may be made to perform traction, extension or bending, or a combination of such actions. FIG. 3 demonstrates an example of a traction-extension combination module, i.e., both gripper and extensor actions in one module.

Figure 67:
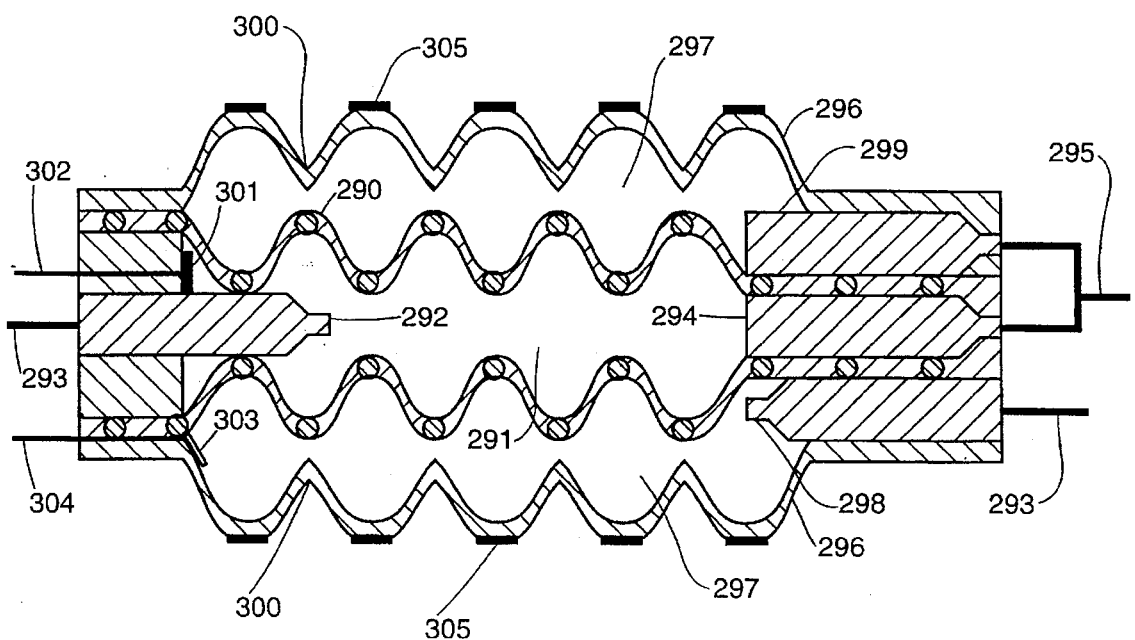
FIG. 67 is a schematically illustrated section view of a gripper-extensor combination module which can undergo passive lateral bending.

Another combined actions module is shown in FIG. 67, which is a section view of a gripper-extensor combination, which can undergo passive lateral bending. An inner, reinforced bellows 290 is inflated by the flow of fluid through a high pressure servovalve 292 from the high pressure source line 293 into the central chamber 291. This inflation causes the module to increase its length as an extensor. The low pressure servovalve 294 is opened when the inner bellows 290 is to be deflated. This action causes the fluid within the central chamber 291 to flow into the low pressure source line 295. An outer balloon 296 is used to grip the inner surfaces of the lumen. The balloon 296 is inflated by the opening of the high pressure servovalve 298 thereby allowing the flow of fluid from the high pressure source line 293 into the outer chamber 297. When the outer chamber is inflated, the balloon 296 is distended to grip the lumen.

When traction is no longer desired, the low pressure servovalve 299 is opened to allow the fluid to flow from the outer chamber 297 into the low pressure source line 295. The balloon 296 is designed to have "pleats" 300 to allow it to easily expand along the axial direction under the action of the inner bellows actuator. The outer surface of the balloon 296 may have traction aids and tactile sensors 305 to measure the loads imposed on the lumen walls. A pressure sensor 301 is connected it to the control electronics. A similar pressure sensor 303 may be utilized to measure the pressure within the outer chamber 297 within the balloon 296.

Figure 68:
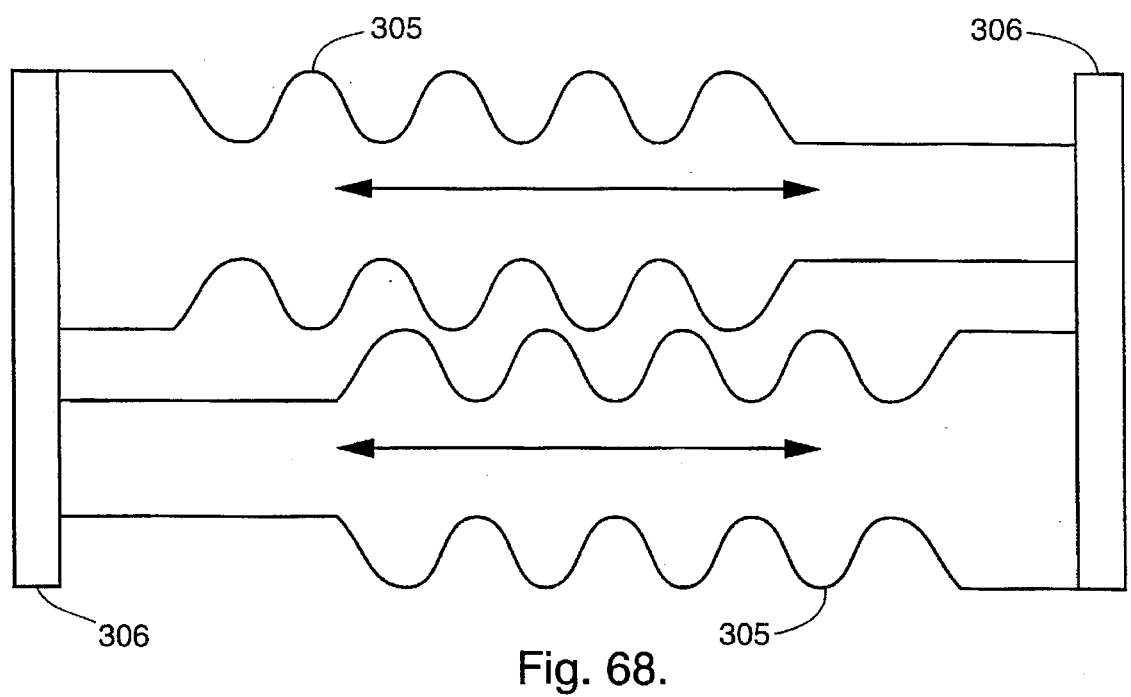
FIG. 68 is a schematic illustration of an extensor-bender combination module.

Certain module embodiments can undergo both extension and bending deformation. One embodiment extensor-bender module, shown in FIG. 68, is a modification of the bender embodiment of FIG. 66. By removing the central link 280, the end plates are allowed to move toward and away from each other. In this case, the shearing loads applied to the mechanism are carried by the linear actuators themselves (this was one job of the central link 280 before). The resulting embodiment, as shown in FIG. 68 has two end plates 306 connected together by a number (two or more) of parallel linear actuators 305. These actuators 305 are shown as bellows, but several different actuation technologies, e.g. shape memory alloys, linear electromagnetic actuation, etc., may be used.

Figure 69:
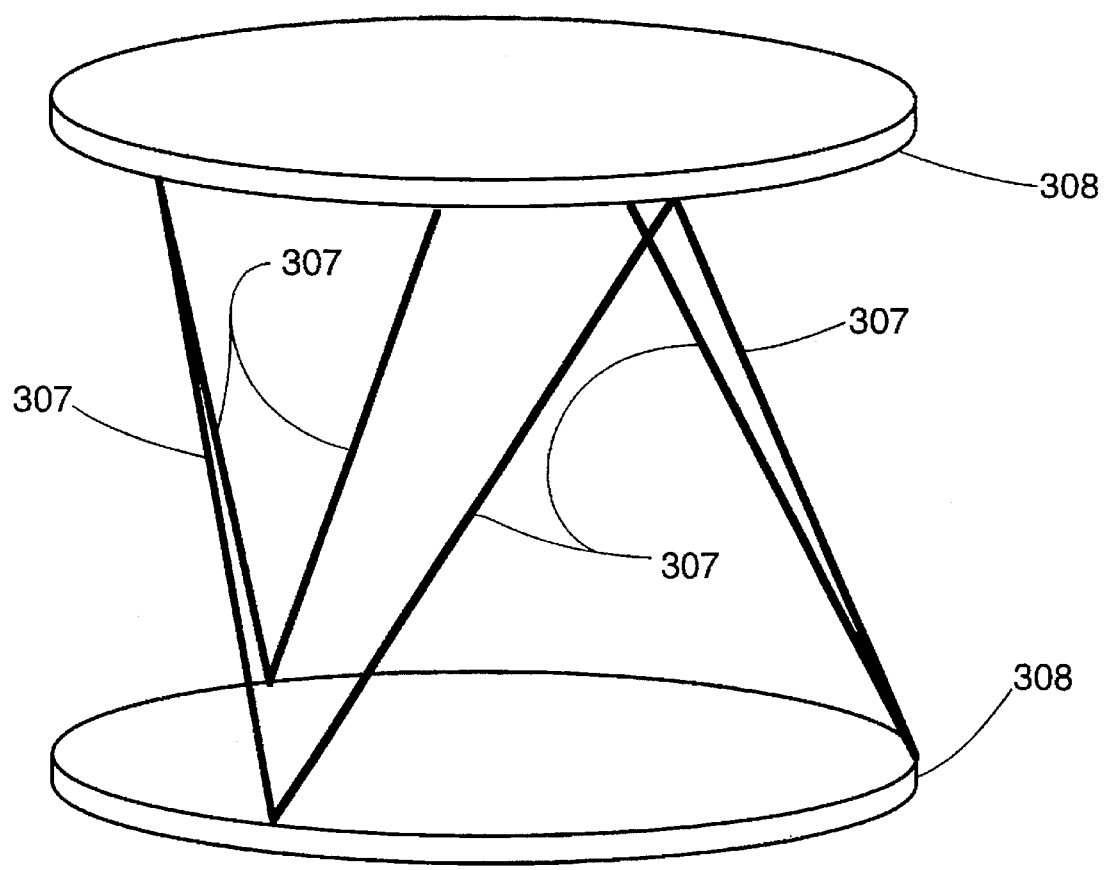
FIG. 69 is a schematic illustration of a Stewart mechanism which can provide for bending and extension.

A Stewart mechanism, as shown in FIG. 69, allows active extension and bending as well as twisting motions of the end plates relative to one another. An extensor-bender module can be made using six linear actuators 307 between the two end plates 308. Similar designs which utilize fewer than six but greater than two linear actuators may also be able to provide adequate combined extension and bending actions. Such designs would sacrifice degrees of kinematic freedom between the end plates for improved simplicity of the mechanical design, control software and electronics.

Figure 70A:
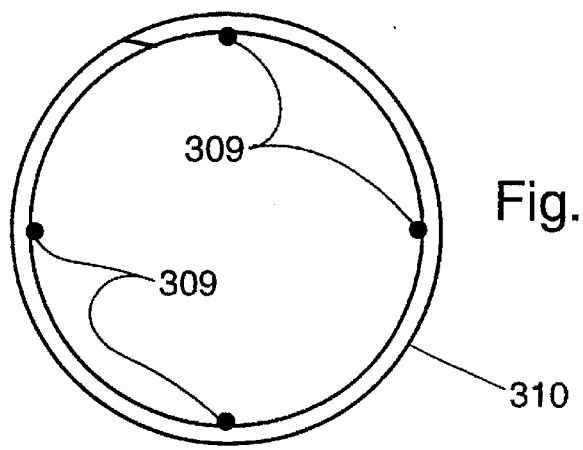
FIG. 70A is an end view thereof.
Figure 70:
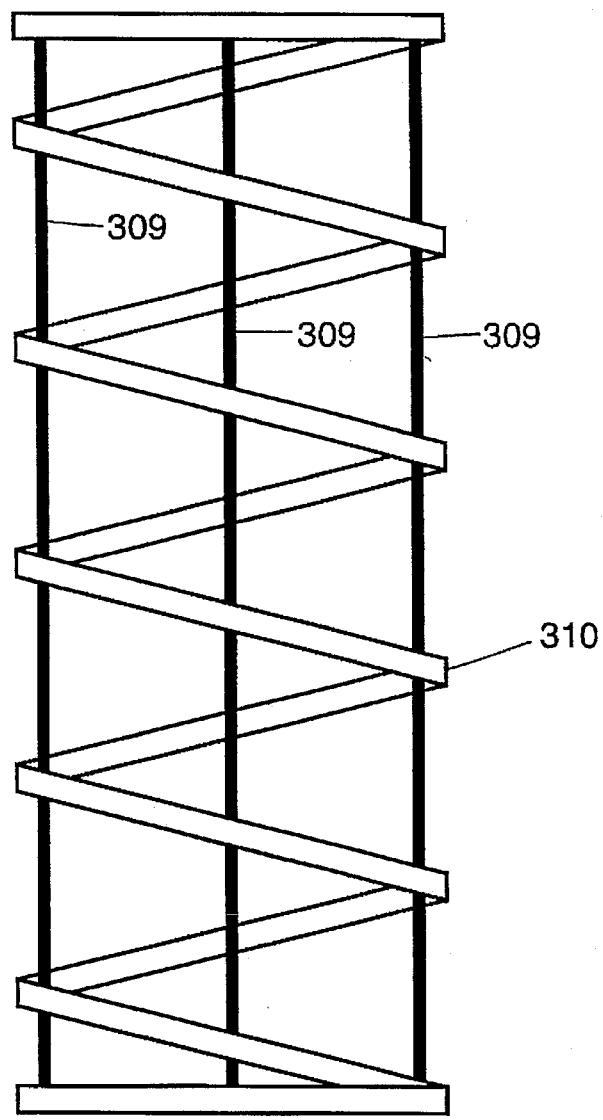
FIG. 70 is a schematic illustration of an alternative embodiment of an extensor-bender combination module actuator.

FIGS. 70 and 70A show another embodiment of an extensor-bender combination module actuator having four shape memory alloy (SMA) wires 309 attached to the inner diameter of a helical spring 310. The SMA wires 309 change their length when they are heated. Such heating can be done merely by sending electrical current through them. Thus, this actuator embodiment can change its length and/or bend as a function of the combined length changes of the driving SMA wires 309. There may be any number of SMA wires 309 to drive this actuator, but if there are fewer than three SMA wires, the module would have reduced kinematic degrees of freedom. A shape memory alloy helical spring may be used as an additional driver of the passive spring 310.

FIGS. 4 and 9 show an embodiment of a module which can produce traction, extension and bending actions. The four inner chambers 101, 102, 103, and 104 can be inflated and deflated singly or multiply to produce desired combinations of extension and bending of the module. The outer balloon 120 can be inflated to grip the inner walls of the lumen thereby producing traction for the module. The sensors and traction aids discussed above can be incorporated into this module embodiment. While the modular construction of the present robotic endoscope from a plurality of segments or modules is preferred, modular construction is not necessary to carry out the invention. For example, the present robotic endoscope may comprise a continuous device having an internal structure divided into segments or regions having the same functions as the modules described above.

Methods For Movement

The various embodiments described above typically have a multiplicity of: (1) devices to grip the lumen wall ("traction devices" or "grippers"); and (2) devices which locally distort the shape of the mechanism via extension/contraction, bending, or a combination of bending and extension ("deformation devices").

By the term "locomotion" we mean the process of generating net displacement of the robotic endoscope inside a flexible lumen via a sequence of gripper and deformation device maneuvers. A "gait" is a distinct cycle of maneuvers that leads to a unit of displacement, which we term a "stride." The length of the displacement is termed the "stride length." Repetition of a gait leads to net displacement, or locomotion. Depending upon the number and arrangement of gripping and deforming mechanisms, a given device will typically be able to implement more than one gait.

The devices described above can implement locomotion that can be categorized into inchworm and concertina movement. These terms are used because the gaits are vaguely analogous to those used by certain species of worms and snakes. However, these methods are not exact analogs of biological motion. Gaits which combine features of both schemes can also be devised.

Inchworm Gaits

A mechanism which can implement an "inchworm-like" gait will have a multiplicity of grippers and a number of deformation devices that can extend and contract their longitudinal dimension (hereafter designed as an "extensors"). The traction and extensor functions may be implemented in separate mechanisms, or in a combined mechanism. An extensor device will typically exhibit passive compliance to lateral motion, in addition to active control of its extension. However, active control of lateral motions is not precluded and may even be desirable.

The Gait of a 2-Gripper 1-Extensor Mechanism

For the purposes of illustration, a locomotion method of a device consisting of two traction mechanisms and one extensor mechanism, as shown in FIG. 71-FIG. 71-7, is first considered. This is a simple arrangement that can generate endoscope locomotion. The traction device is represented as an expandable balloon. However, any of the expanding traction device embodiments previously discussed can be employed. Likewise, the extensor mechanism is depicted as a pneumatic bellows, though any other extensor mechanism can be similarly employed. The lumen is represented as a straight wall tube. However, the schemes will work if the lumen is curved and has reasonable variations in its cross-section shape and diameter.

This device can implement only one gait. The sequencing of the gait for forward motion proceeds as follows (in FIG. 71 forward motion means motion to the right). The aft traction device 400 is expanded to grip the lumen wall (as indicated in FIG. 71-1). Meanwhile the forward gripper 402 and the extensor 401 are in their retracted states. The extensor device 401 is then extended (FIG. 71-2). While the extensor will typically be expanded to its full length, partial extension is possible. If the lumen is curved, the lateral compliance (active or passive) of the extensor will cause the expanding extensor to move in the principle direction of the lumen. After the extension is complete, the forward traction device 402 is expanded to grip the lumen wall (FIG. 71-3). After the forward gripper 402 has extended, the rear gripper 400 is retracted (FIG. 71-4). Next, the extensor 401 is retracted (FIG. 71-5). Here again, the extensor will typically be retracted to its shortest position, though partial retraction is possible. Subsequently, the rearward gripper 400 is expanded to grip the lumen wall (FIG. 71-6). Finally, the forward gripper 402 is retracted (FIG. 71-7). At this point, the device is in the same state as the beginning of this sequence (FIG. 71-1) and the movement cycle is complete. However, the endoscope has moved forward by a single stride length. In this case, the stride length is the difference between the extended extensor length (FIG. 71-2), and the retracted extensor length (FIG. 71-5).

These steps comprise a single gait cycle which cycle can be repeated to provide continual motion. This cycle can also be reversed to implement motion in the rearward, or opposite, direction.

Gaits for a 3-Gripper/2- Extensor Mechanism

Figures 7, 75:
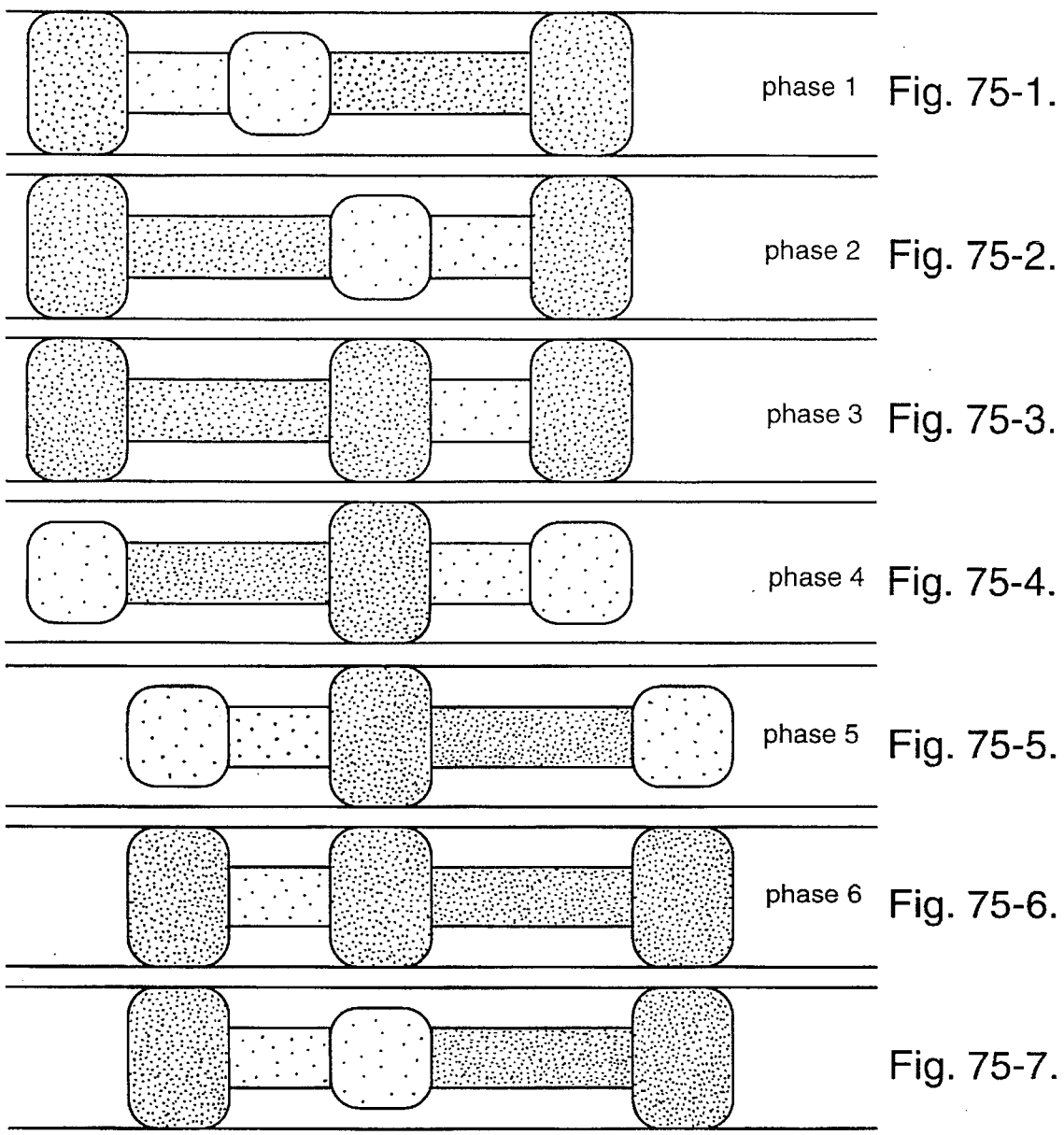

FIG. 72 through FIG. 72-10 shows locomotion of a 3 gripper and 2 extensor embodiment. This embodiment can effect at least nine distinct gaits. By way of example, two of these gaits are shown and described. Schematics of other gaits for a 3-gripper/2-extension mechanism are included in FIGS. 74 and 75.

Initially, all of the grippers and extensors are in their expanded states (FIG. 72-1). The rear gripper 403 is retracted (FIG. 72-2). Next, the rear extensor 404 is retracted, either partially, or fully (FIG. 72-3). If the lumen is curved, passive (or active) lateral compliance of the extensor allows for movement in the principal direction of the curved lumen. Subsequently, the rear gripper 403 is expanded to make contact with the lumen (FIG. 72-4). The middle gripper 405 is then retracted (FIG. 72-5). The rear extensor is expanded and the front extensor contracts (FIG. 6), shifting the middle gripper forward. The middle gripper then expands (FIG. 7). The forward gripper 407 is retracted, and then the forward extensor is extended (FIGS. 72-8 and 72-9). Finally, the forward gripper 407 is again expanded (FIG. 72-10). At this point the mechanism has returned to its original state, but moved forward by one stride length. This cycle can be repeated for continual forward movement, or it can be reversed for rearward motion.

From the explanation of this gait sequence, it can be seen that contact points with the lumen advance along the lumen wall in a "wave-like" pattern. Hence, this motion sequence can be described as a "traveling wave gait." With this gait, at least 2 gripping devices actively make contact with the lumen. Thus, the three gripper device employing this gait is able to better grasp the lumen than the 2 gripper design of FIG. 71.

FIG. 73 shows a second example of distinct gait for a 3-gripper/2-extensor device. In its initial state (FIG. 73-1), the rear and middle grippers 403, 405 are expanded, while the forward gripper 407 is retracted. Then, the forward extensor 406 is fully or partially extended (FIG. 73-2). Next, the forward gripper 407 is expanded to establish contact with the lumen wall (FIG. 73-3). The rear 403 and middle 405 grippers are retracted (FIG. 73-4). Next, the forward extensor 406 is retracted fully or partially (FIG. 73-5). Then, the rear 403 and middle 405 grippers are extended (FIG. 73-6). Finally, the forward gripper 407 is retracted, leaving the mechanism in its original state (FIG. 73-7). Here again, this gate can be repeated for continual motion, or used in reverse.

In all phases of this gait, the rear extensor 304 is retracted. The same sequence of maneuvers could also be used if the rear extensor were extended. In other words, this gait makes no use of the rear extensor. Thus, if the rear extensor 404 were to become inoperable during use, this gait could be used to enable endoscope locomotion. Similarly, other gaits may be derived which will be unaffected by the failure of extensor 406. Hence, because the endoscope can switch between gaits, this design is robust to extensor failure. In addition, one can also derive a gait which will be robust to the failure of one of the grippers (assuming that the gripper fails in its retracted state).

Figure 76:
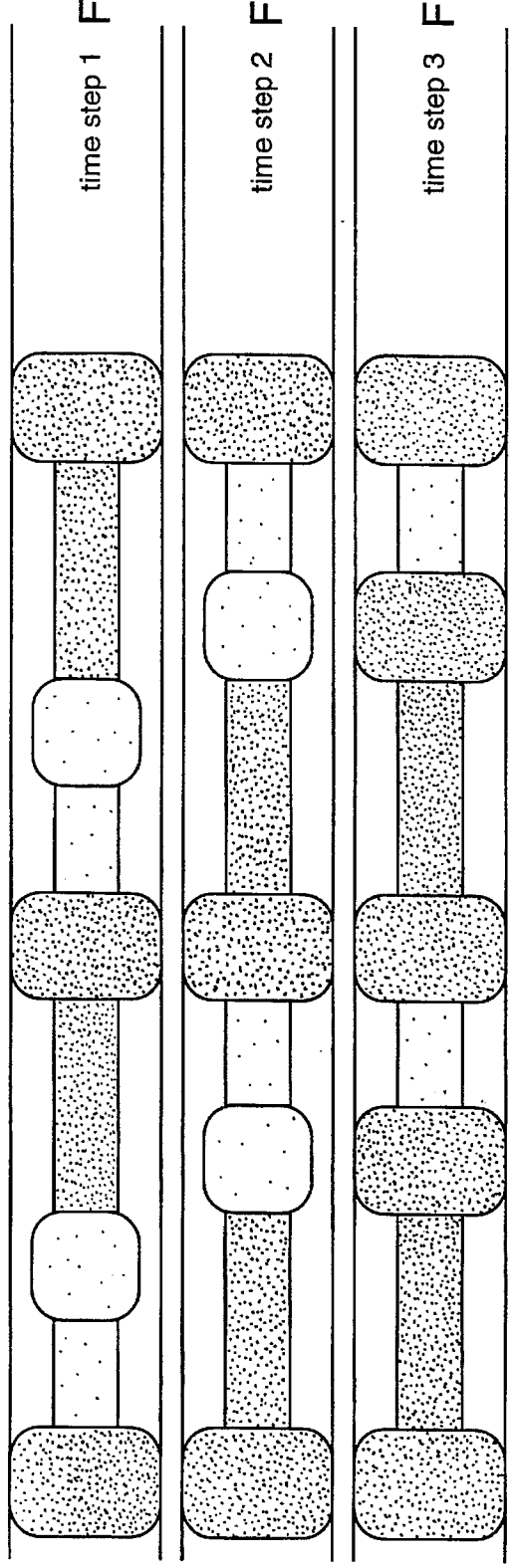
Figures 7, 76:
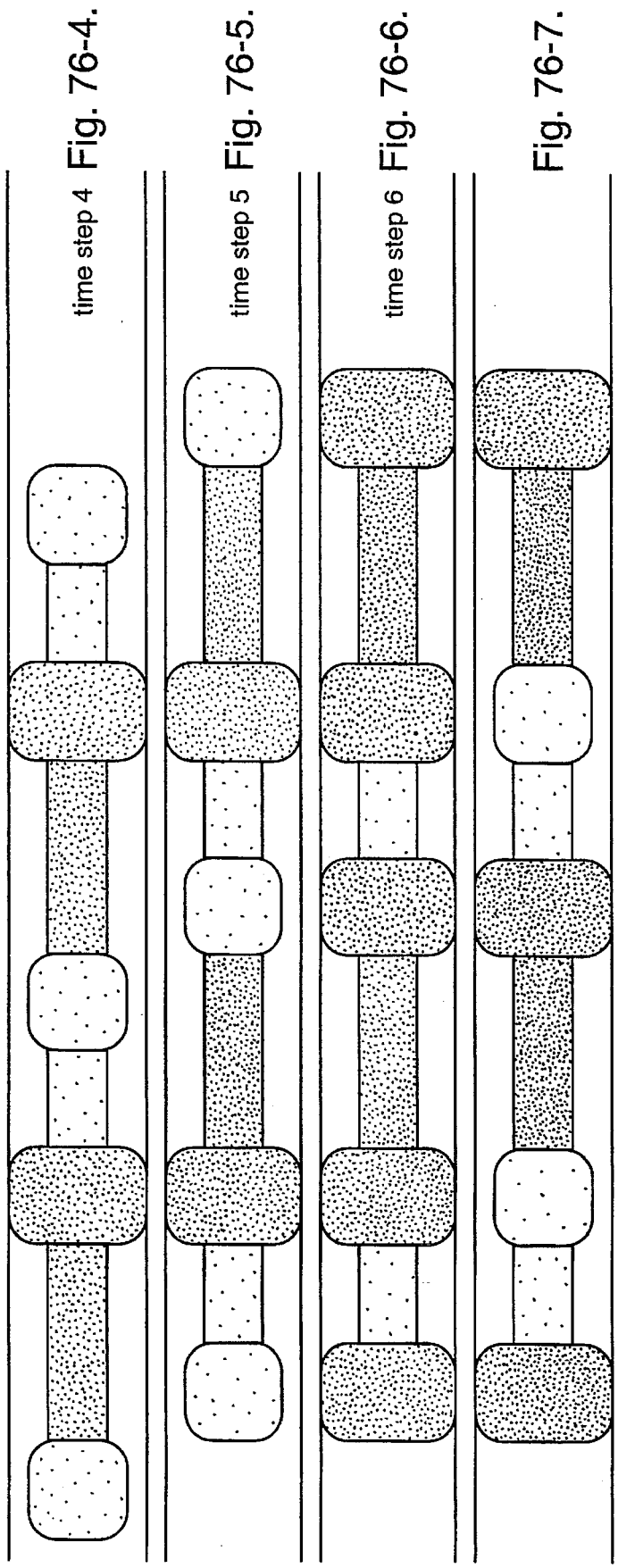

Gaits for Embodiments Consisting of a Multiplicity of Grippers and Extensors As the number of grippers and extensors used to implement the robotic endoscope increases, the number of possible gaits increases as well. For example, FIGS. 76, 77 and 78 show a few possible gaits for a device consisting of 5 grippers and 4 extensors. We do not list here all possible gaits for all possible combinations of extensors and grippers. However, for a given device, it will be evident to those skilled in the art that one can systematically develop the sequencing of all possible gaits, based on the foregoing description.

In general, it is advantageous for an endoscope implementation to be capable of a large number of gaits. As shown above, some gaits typically have more grippers in contact with the lumen. These gaits tend to be more stable, though the progress of the device through the lumen tends to be slower. Other gaits are robust to the failure of particular components, as illustrated in FIG. 73. The present endoscope has the ability to switch between gaits to accommodate changing conditions within the lumen, or to the endoscope itself. The endoscope gaits can be changed by the user, by sending commands to the locomotion control electronics.

Concertina-Like Gaits

In another embodiment, the deformation segments have the ability to actively control their lateral bending (such as those of FIGS. 4 and 9). With these segments, "concertina" gaits may be used. For the concertina gait, the endoscope embodiment includes a multiplicity of deformation modules which can actively control lateral bending ("lateral deformers"). The deformation modules may also implement extension and contraction as well, though it may not be critical to this gait. Each of the lateral deforming modules may also contain a lumen gripping device (such as an expandable balloon) described above. However, the concertina gait may be implemented without such gripping devices.

Figure 12:
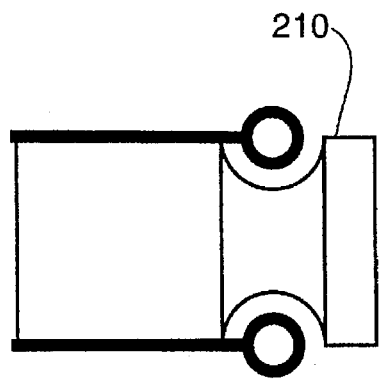
FIG. 12 is a schematically illustrated side elevation view of an alternative traction module embodiment in the contracted position.
Figure 13:
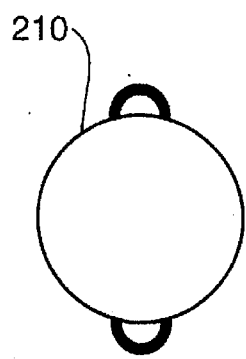
FIG. 13 is an end view thereof.
Figure 14:
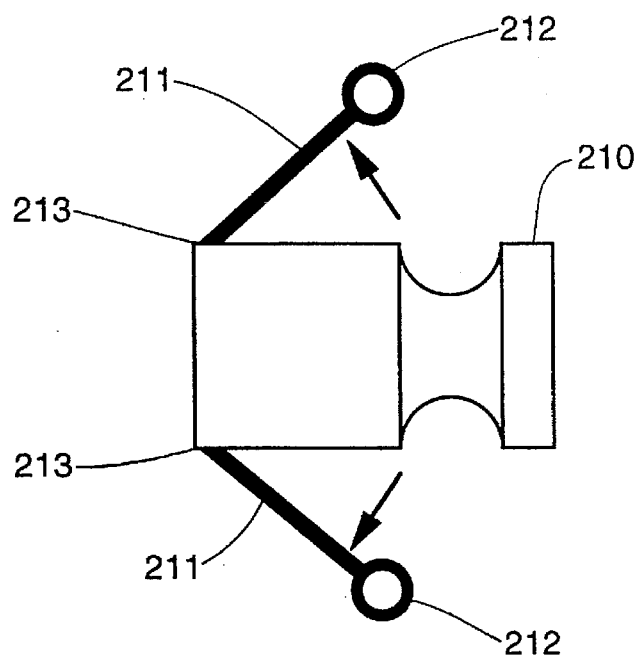
FIGS. 14 and 15 show the traction module of FIGS. 12 and 13, in the extended position.
Figure 15:
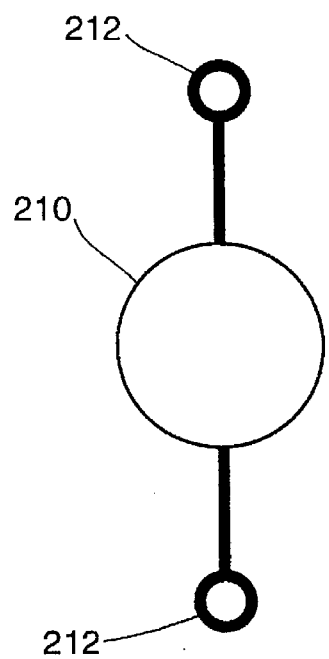
Figure 16:
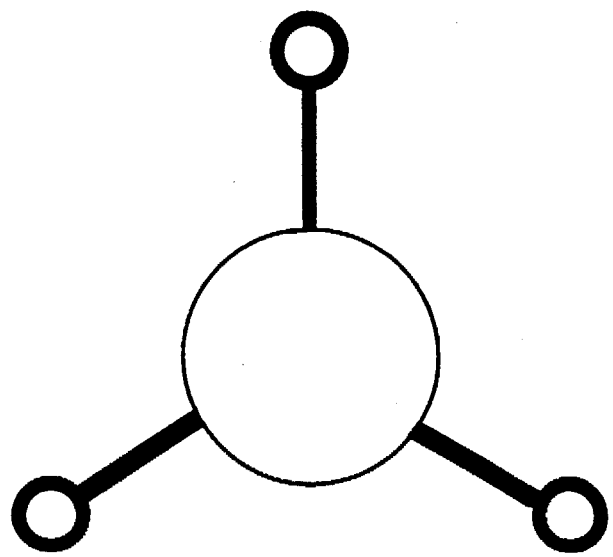
FIGS. 16 and 17 are end views of other alternative embodiments of traction modules.
Figure 17:
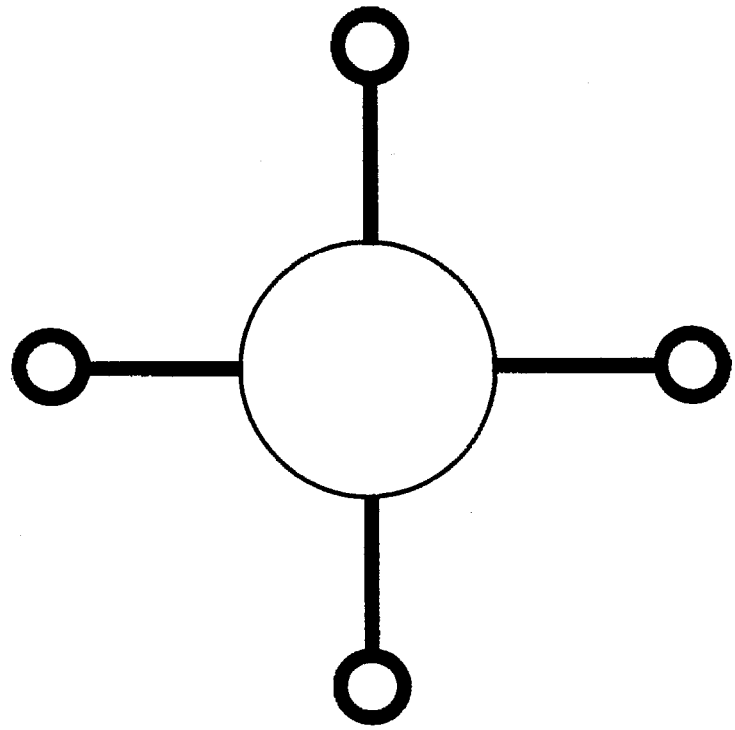
Figure 18:
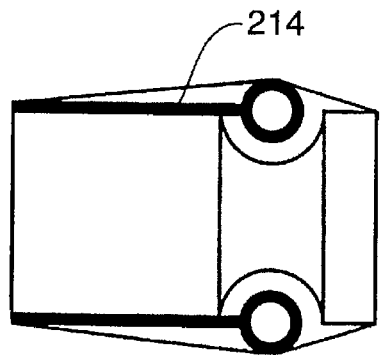
FIG. 18 is a schematically illustrated side elevation view of a traction module similar to the traction module of FIG. 12, in the contracted position, but further including a sheath.
Figure 19:
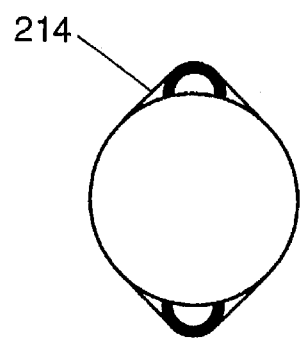
FIG. 19 is an end view thereof.
Figure 20:
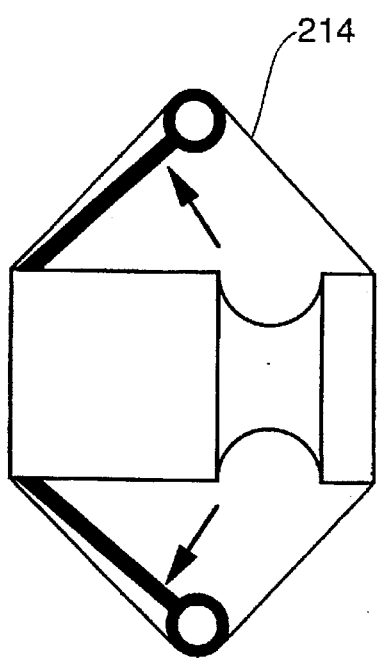
FIGS. 20 and 21 are show the traction module of FIGS. 18 and 19 in the expanded position.
Figure 21:
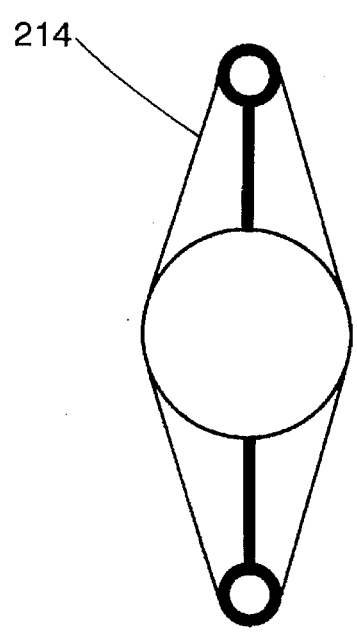
Figure 22:
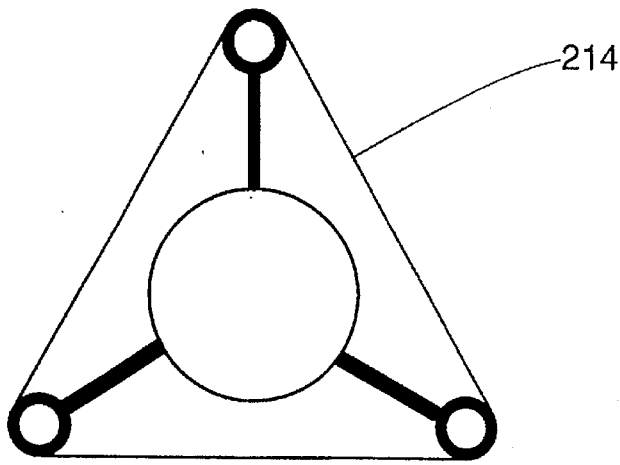
FIGS. 22 and 23 are end views of alternative embodiments similar to the traction module of FIG. 16, and further including a sheath.
Figure 23:
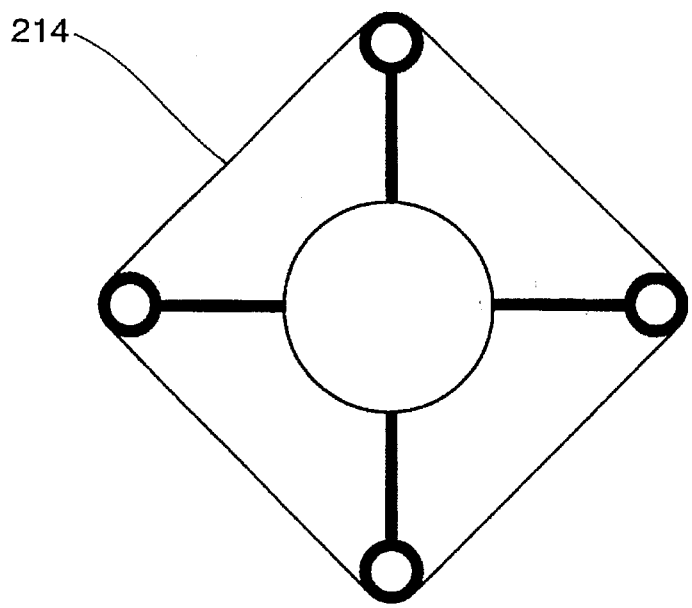
Figure 24:
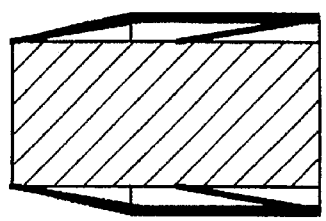
FIG. 24 is a schematically illustrated side elevation view of another alternative traction module embodiment having cylindrical shells, in the contracted position.
Figure 25:
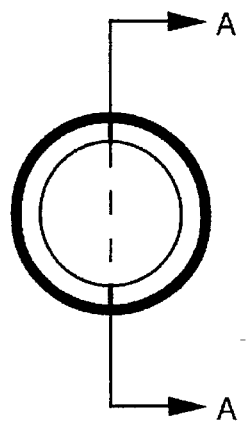
FIG. 25 is an end view thereof.
Figure 26:
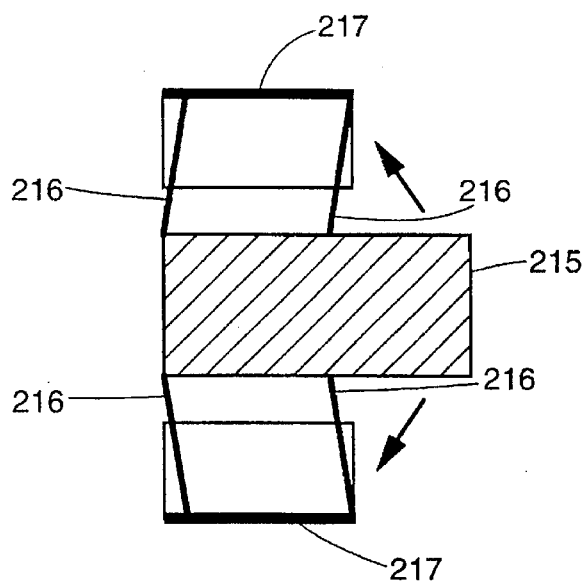
FIGS. 26 and 27 show the traction module of FIGS. 24 and 25 in the extended position.
Figure 27:
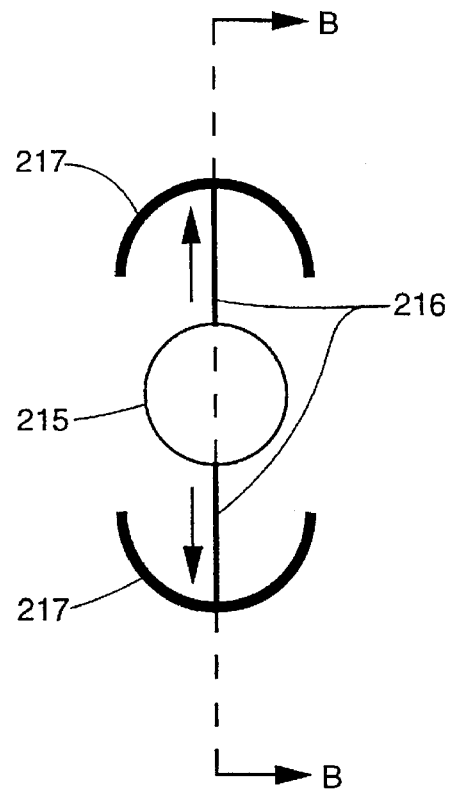

FIG. 79-1 through 79-12 are cut-away schematic views of the lumen, showing the sequence of endoscope maneuvers in a concertina gait. The lumen shown is straight, but the method will work for curved lumens as well. Each segment in FIGS. 79-1 through 79-12 is a lateral deformer of the type described above. While 19 such segments or modules are shown, various numbers can be used. For clarity of illustration, trailing cables, biopsy arms, or other features of the device which are not essential to understanding its locomotion behavior, are omitted.

The endoscope starts in an undeformed position (phase 1, FIG. 79-1). To initiate locomotion, segments or modules just aft of the front (e.g., television camera) segment are bent to form a "loop." The bending is increased until one or more points of the loop contact the lumen (phase 2, FIG. 79-2). These contacts could be directly on the exterior (or skin) of the lateral deforming modules. Alternatively, any of the aforementioned gripping aids could be added to the lateral deformer module to enable effective contact with the lumen wall. The number of segments involved in the formation of the loop will depend upon the width of the lumen. As the loop may be formed of several segments, the concertina gait can be advantageously used in large lumens, or in lumens with large variations in size.

Next, the segments aft of the first loop are bent in the opposite direction to form a second loop that makes contact with the lumen (phase 3, FIG. 79-3). Subsequently, segments are deformed to form alternating loops that make contact with the lumen wall, until there remain no undeformed segments (phase 4, FIG. 79-4). The endoscope is then "fully contracted". The effective length of the endoscope is substantially shortened, while its effective width is significantly increased, when it is fully contracted. The front segment of the endoscope, (which may contain the viewing apparatus) is pointing forward. Hence, a useful view of the lumen is maintained during this initial positioning phase. This fully contracted state is the initial state for the repetitive concertina gait sequence.

To proceed forward, the lateral deformer segments comprising the forward loop are straightened. This action effectively pushes the front segment forward through the lumen (phase 5, FIG. 79-5). Subsequently, the next loop is straightened, further pushing the distal segment forward (phase 6, FIG. 79-6). This process of straightening the leading loop segments continues until 3 or 4 of the most rearward loops remain in contact with the lumen wall (phase 7, FIG. 79-7). At this point, the most forward lateral deforming segments (behind the front segment) begin deforming again to form a forward loop. Meanwhile, the process of straightening the rearward loops continues in parallel (phase 8, FIG. 79-8). Next, the segments just behind the newly formed forward loop, also form a loop, while the segments of the forward most rear loops simultaneously straighten. This process continues until all of the rearward loops have been straightened (phases 9 and 10, FIGS. 79-9 and 79-10). This process of forming and straightening the endoscope loops must be carried out simultaneously if the lateral bending segments have no capability to extend their length. Otherwise, the constraint of constant endoscope length will be violated. If the lateral bending segments can extend or contract, then the loop forming and straightening process might be carried out asynchronously, with extension/contraction of one or more of the deforming segments being used to take up the slack.

Next, undeformed segments behind the rearward most loop are laterally deformed to form yet another loop (phase 11, FIG. 79-11). Subsequently, additional segments form alternating loops, until the mechanism again reaches its fully contracted state (phase 12). Hence, the endoscope has returned to the same state as that of phase 4, but is now translated forward in the lumen by one stride length. The cycle consisting of phases 4 through 11 can then be repeated to provide continual motion via the concertina gait. Or, the process can be reversed to provide backwards motion.

This gait has two notable characteristics. First, the endoscope always maintains at least 3 or 4 contacts with the lumen wall. This is required to maintain stable positioning of the endoscope with respect to the lumen. Second, the maneuvering of the lateral bending units into the "loops" effectively increases the cross section of the endoscope. The size of the loops formed by the lateral deformers can be adjusted by choosing the amount of lateral deformation and the number of segments involved in the loop. Hence, this embodiment of the endoscope can handle lumens of widely varying diameter by adjusting the size of the loops which are used to implement the concertina gait.

Combined Gaits

The described gaits are not the only ones that can be implemented with the mechanical embodiments shown. Inchworm and concertina gaits may be used separately, or in combinations. Many possible implementations of the robotic endoscope may include a combination of gripping devices with a mixture of deformation devices that may have extensor and/or lateral bending capability. A multiplicity of gaits using such combinations may be used. For example, one possible combination gait is shown in FIG. 80.

In this gait, a concentration of several lateral bending modules forms a sequence of alternating loops, akin to the loops of the concertina gait. The outermost point of each of these loops makes contact with the lumen. In effect, this sequence of loops forms a gripping device which can grip lumens with widely varying diameter and geometry. An embodiment using this method would require at least two such sequences of bending devices, since at least two gripping mechanisms are required to effect endoscope motion. These looping subsystems are connected by one or more extensor modules. Thus, this system can implement inchworm-like gaits, where the extensor modules operate in the same fashion as an inchworm gait, and the bending modules operate as gripping devices.

System Aspects

The mechanical device embodiments described above are components of an overall robotic endoscope design. There are various ways to coordinate the actions of the individual components and subsystems into the overall design. Some or all of these system components may be employed in different embodiments of the present endoscope.

User Interface

A physician or surgeon controls the robotic endoscope via an electronic interface. This interface may include a joystick, computer keyboard, graphical user interface, heads-up-display, or some combination of these devices. This interface may provide a means to display or relate information regarding the status of the endoscope's operation, and a display for information gathered by the many possible on-board diagnostic sensors and video system. The interface may also provide a way for the endoscope user to command various aspects of the endoscope's 's operation. Much of the operation of the interface can be controlled by computers.

Locomotion Control Subsystem

The present robotic endoscope can move in a flexible lumen using a variety of maneuvers, or "gaits," as described above. In use, the control of the gait maneuvers will be provided by an electronic, or computer system. In addition to controlling the proper sequencing of module movement, the locomotion control system also interprets the physician's inputs that relate to movement of the device. These inputs are used to adjust various parameters which are involved in the sequencing of the gaits. For example, inputs from the endoscope user can be used to change the speed with which the endoscope moves in the lumen, reverse the endoscope's direction, or stop the endoscope's movement.

Many embodiments of the endoscope can implement more than one gait. Hence, the locomotion control system may also manage the selection of a gait. The choice of gait may be a parameter that can be controlled by the endoscope user, via the user interface. In some cases, it may be desirable for the locomotion control system to automatically select a gait that is most suited to a given situation. In other possible embodiments, it may also be useful for the endoscope user to over-ride the control system's automatic choice of gaits.

The computer which controls the endoscope's movement can have many physical embodiments. As shown in FIG. 1, the computer which coordinates the movement of the gripping and deformation devices can consist of a single computer 56 located inside any one of the endoscope modules. This computer will communicate with various modules and sensors via specialized busses as described below. The locomotion control may also be implemented by a multiplicity of controllers, with one controller located in each endoscope module. Alternatively, the entire sequencing of endoscope maneuvers can be regulated by an external computer which communicates with the endoscope modules and on board sensors via a tether or cable. Locomotion control may be effected by a combination of onboard computers and externally sited computers which communicate via busses, as described below. The computer or computers which control the endoscope's locomotion may also be able to control other aspects of the endoscope's operation.

Bus Subsystems

Various bus systems may be used. A pneumatic or hydraulic bus includes a high pressure and low pressure fluid supply (such as air, $CO_2$, water, saline, hydraulic fluid, etc.) which can be used to activate actuators in the modules and to provide compressed gas for possible irrigation, insufflation and suction devices located on the endoscope. This bus is connected to the trailing tether 16, as shown in FIG. 1. A control bus includes means to pass control and sensor signals throughout the modules. For example, in some embodiments, the bus may be physically located as is the bus 107 in FIG. 4, or as the bus 52 in FIGS. 1 and 3. A sensor bus as a separate electrical bus, may be preferable in some embodiments. The sensor bus includes one or more wires, to transmit signals from the various possible medical sensors on the endoscope. In some embodiments, it may be necessary to distribute power to the various modules, sensors, cameras, and controllers via a power bus. Power can be provided to the power bus from an onboard energy storage medium (such as batteries), or via a trailing cable. In other embodiments, energy can be transmitted to the device via electromagnetic radiation. A video bus includes an electrical or fiber optic system that can transmit signals from one or more onboard video cameras throughout the endoscope system. The implementation of these busses may take various forms, depending upon which of the characteristics of the embodiments may be used.

Communications and Telemetry Subsystems

It will often be necessary for signals which are generated by onboard sensors, video cameras, and controllers to be transmitted off board of the endoscope. For example, it will often be desirable to transmit information from the onboard sensors to the user interface, where the signals are processed and presented to the endoscope user. Likewise, in many applications, external signals must be transmitted to the endoscope's onboard electronics. For example, in some embodiments, the locomotion control computer is physically located within the endoscope. Commands from the endoscope user must be relayed to the locomotion controller for safe and efficient operation. In certain applications, more than one robot endoscope unit may be used. For example, a series of robotic endoscopes, operating in a manner that is analogous to a system of tugboats, could pull a fiber optic cable into a lumen for the purposes of laser surgery. It may be desirable to transmit signals from one unit to another. Thus, communication to and from the endoscope is desirable. The signals from the aforementioned control, sensor, and video busses may be connected to the communication system for simplified transmission of these signals.

Communications may be made over tethers and radio telemetry. Tethers may be electrical wires or fiber optic cables with an individual wire or fiber optic cable referred to as a "communication channel." In some embodiments, it may be preferred to assign one signal per communication channel. In other embodiments, it may be preferred to multiplex signals on communication channel, thereby reducing the number of communication channels. While a communications tether will typically trail behind the endoscope device, and may often be intertwined with other trailing cables (such as the compressed gas hose 16 of FIG. 1, a communications tether may also be connected to the front of the endoscope unit for the purposes of communication and coordination with other endoscope robot units operating within a lumen. In other embodiments, the function of these communication tethers could be replaced by radio telemetry, such as the receiver/transmitter 56 in FIG. 1.

Thus, although several embodiments have been shown and described, it would be obvious to those skilled in the art that many modifications to the present robot are possible, without departing from the spirit and scope of our invention.

What we claim is:

1. A robotic endoscope comprising:
    a first traction module;
    an extensor module attached to the first traction module;
    a second traction module attached to the extensor module;
    each of the first and second traction modules including a central module body, and a cylindrical shell having a traction surface, with the cylindrical shell displaceable from the central module body;
    the first and second traction modules having means for moving the cylindrical shell outwardly from the central body module; and
    the extensor module having means for increasing and decreasing its length.

2. The robotic endoscope of claim 1 wherein the means for moving a traction surface comprises a hydraulic or pneumatic actuator.

3. The robotic endoscope of claim 2 wherein the pneumatic or hydraulic actuators are controlled by valves in the traction modules.

4. The robotic endoscope of claim 1 wherein the means for moving a traction surface comprises internal balloons inflatable pneumatically or hydraulically.

5. The robotic endoscope of claim 1 wherein the means for moving the traction surfaces comprises an electromagnetic actuator.

6. The robotic endoscope of claim 1 wherein the means for moving the traction surface comprises shape memory alloy actuators.

7. The robotic endoscope of claim 1 wherein the means for moving a fraction surface comprises a magnetostrictive material actuator.

8. The robotic endoscope of claim 1 wherein the means for moving the traction surface comprises piezoelectric material actuators.

9. The robotic endoscope of claim 1 further comprising and outer sheath overlying the traction and extensor modules, including the cylindrical shells.

10. The robotic endoscope of claim 1 further comprising a force sensor on a traction module for measuring forces applied to lumen walls.

11. A robotic endoscope comprising:
    a first traction module;
    an extensor module attached to the first traction module, within a plurality of inflatable balloons circumferentially arranged with the extensor module;
    a second traction module attached to the extensor module;
    a traction surface on the outside of each of the traction modules; and means for moving the traction surface outwardly from the traction modules to engage a lumen around the traction modules.

12. The robotic endoscope of claim 11 further comprising internal pressure sensors on the traction modules for measuring outward movement of the traction surface.

13. A robotic endoscope comprising:

a first traction module;

an extensor module attached to the first traction module and having means for increasing and decreasing its length;

a second traction module attached to the extensor module;

the first and second traction modules each having at least two oar-like protuberances pivotably attached thereto;

each oar-like protuberance having a traction surface for engaging a lumen;

means for pivoting the oar-like protuberances.

14. An endoscope comprising:

a plurality of modules linked together, with at least one of the modules including:

a central core;

a multiplicity of inflatable sacs circumferentially located around the central core; and a balloon overlying the central core and inflatable sacs.

15. The endoscope of claim 14 wherein the balloon is toroidal.

16. The endoscope of claim 14 further comprising valves for inflating and deflating the sacs and the balloon.

17. A robotic endoscope comprising:

a first traction module;

an extensor module attached to the first traction module;

a second traction module attached to the extensor module;

traction surfaces on the first and second traction modules;

the traction modules having means for moving their traction surfaces outwardly to engage a lumen around the module;

the extensor module including a bellows forming the outside surface of the extensor module, and forming a central chamber and a spring within the bellows extending laterally entirely across the central chamber.

18. The robotic endoscope of claim 17 further comprising servo valves for controlling fluid to the bellows.

19. The robotic endoscope of claim 17 further comprising a computer for controlling locomotion of the robotic endoscope, located within one of the modules.

20. An endoscope comprising:

a plurality of modules linked together, with at least one of the modules including:

a module body;

a balloon around the outside of the module body;

a high pressure valve in the module body, positioned between a high pressure source line extending through the module body, and the balloon; and a low pressure valve in the module body, positioned between a low pressure source line extending through the module body, and the balloon.

21. The endoscope of claim 20 further comprising a tactile sensor on an outer surface of the balloon.

22. The endoscope of claim 21 further comprising an internal pressure sensor on the module body and within the balloon.

23. The robotic endoscope of claim 20 further comprising an outer sheath substantially continuously overlying the traction and extensor modules.

24. An endoscope comprising:

first and second traction modules;

an extensor module attached to the first and second traction module, the extensor module having means for increasing and decreasing its length; and bow wires on the traction modules, the bow wires displaceable from a relaxed position generally alongside the traction module, to an extended position wherein the bow wires are bowed out in arc.

25. A robotic endoscope comprising:

a first traction module having a traction surface;

an extensor module attached to the first module and having means for increasing and decreasing its length;

a second traction module having a traction surface and attached to the extensor module;

the traction modules having means for moving their traction surfaces outwardly to engage a lumen; and an outer sheath substantially continuously overlying and covering the traction modules and the extensor module.

* * * * *